US006875604B2

(12) United States Patent
Shin et al.

(10) Patent No.: US 6,875,604 B2
(45) **Date of Patent: *Apr. 5, 2005**

(54) THERMAL CYCLING DEVICE WITH MECHANISM FOR EJECTING SAMPLE WELL TRAYS

(75) Inventors: Hon Siu Shin, Singapore (SG); Jew Kwee Ngui, Singapore (SG)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/642,418

(22) Filed: Aug. 14, 2003

(65) Prior Publication Data

US 2004/0033592 A1 Feb. 19, 2004

Related U.S. Application Data

(63) Continuation of application No. 10/199,470, filed on Jul. 22, 2002, now Pat. No. 6,638,761, which is a continuation-in-part of application No. 09/496,408, filed on Feb. 2, 2000.

(51) Int. Cl.[7] .................................................. C12M 1/34

(52) U.S. Cl. ............................... 435/287.2; 435/257.3; 435/288.4; 435/809; 422/63; 422/65; 422/102; 436/809; 219/428; 219/385; 219/433

(58) Field of Search ........................... 422/63, 65, 101, 422/102, 104; 435/91.2, 287.2, 287.3, 288.4, 809; 436/809; 219/428, 385, 433

(56) References Cited

U.S. PATENT DOCUMENTS

| | | | | | |
|---|---|---|---|---|---|
| 3,080,759 | A | * | 3/1963 | McQuaid | 73/863.73 |
| 3,634,651 | A | | 1/1972 | Siegell et al. | |
| 3,933,165 | A | * | 1/1976 | Budzak et al. | 137/625.48 |
| 4,094,641 | A | | 6/1978 | Friswell | |

(Continued)

FOREIGN PATENT DOCUMENTS

| | | | | |
|---|---|---|---|---|
| DE | 195 01 298 | C1 | | 2/1996 |
| DE | 19739119 | A1 | * | 3/1999 |
| EP | 0 379 437 | B1 | | 5/1993 |
| EP | 0 542 422 | A1 | | 5/1993 |
| EP | 0 606 534 | B1 | | 7/1994 |
| EP | 0 810 030 | B1 | | 12/1997 |
| EP | 0 810 030 | A1 | | 12/1997 |
| EP | 0 836 884 | A2 | | 4/1998 |
| EP | 0895240 | A1 | * | 2/1999 |
| EP | 0955097 | A1 | * | 11/1999 |

(Continued)

OTHER PUBLICATIONS

D.C. Uber et al., "Application of Robotics and Image Processing to Automated Colony Picking and Arraying," *BioTechniques*, vol. 11, No. 5, 642–644 (1991).

Peter Jones et al., "Integration of Image Analysis and Robotics into a Fully Automated Colony Picking and Plate Handling System," *NucleidAcids Research*, vol. 20, No. 17, 4599–4606 (1992).

(Continued)

*Primary Examiner*—David A. Redding

(57) ABSTRACT

A thermal cycling device for biological samples. The thermal cycling device may include a sample block, an annular plate, and a plurality of spring devices interposed between the sample block and the annular plate. The sample block has a plurality of openings for receiving sample wells of a sample well tray. The annular plate may be positioned adjacent the outer periphery of the sample block and may be configured to abut a bottom surface of the sample well tray when the sample well tray is positioned thereon. The plurality of spring device may be interposed between the sample block and the annular plate to urge the annular plate and sample well tray away from the sample block.

17 Claims, 22 Drawing Sheets

U.S. PATENT DOCUMENTS

| | | | | | |
|---|---|---|---|---|---|
| 4,096,965 | A | | 6/1978 | Lessnig et al. | |
| 4,909,992 | A | | 3/1990 | Björkman | |
| 4,948,564 | A | * | 8/1990 | Root et al. | 422/101 |
| 5,030,418 | A | | 7/1991 | Miyata | |
| 5,159,197 | A | | 10/1992 | Wannlund | |
| 5,210,015 | A | * | 5/1993 | Gelfand et al. | 435/6 |
| 5,282,543 | A | | 2/1994 | Picozza et al. | |
| 5,346,672 | A | | 9/1994 | Stapleton et al. | |
| 5,378,433 | A | | 1/1995 | Duckett et al. | |
| 5,459,300 | A | | 10/1995 | Kasman | |
| 5,464,541 | A | * | 11/1995 | Aysta et al. | 210/767 |
| 5,475,610 | A | * | 12/1995 | Atwood et al. | 700/269 |
| 5,539,848 | A | * | 7/1996 | Galloway | 385/89 |
| 5,582,665 | A | | 12/1996 | Eigen et al. | |
| 5,602,756 | A | * | 2/1997 | Atwood et al. | 700/269 |
| 5,604,130 | A | | 2/1997 | Warner et al. | |
| 5,616,301 | A | * | 4/1997 | Moser et al. | 422/104 |
| 5,681,492 | A | | 10/1997 | Van Praet | |
| 5,710,381 | A | * | 1/1998 | Atwood et al. | 73/864.91 |
| 5,721,136 | A | | 2/1998 | Finney et al. | |
| 5,741,463 | A | | 4/1998 | Sanadi | |
| 5,780,717 | A | * | 7/1998 | Wise et al. | 73/23.2 |
| 5,928,907 | A | * | 7/1999 | Woudenberg et al. | 435/91.2 |
| 6,015,674 | A | * | 1/2000 | Woudenberg et al. | 435/6 |
| 6,159,368 | A | * | 12/2000 | Moring et al. | 210/321.75 |
| 6,162,400 | A | * | 12/2000 | Schembri | 422/72 |
| 6,190,619 | B1 | | 2/2001 | Kilcoin et al. | |
| 6,197,572 | B1 | * | 3/2001 | Schneebeli | 435/286.2 |
| 6,251,662 | B1 | | 6/2001 | Day | |
| 6,272,939 | B1 | * | 8/2001 | Frye et al. | 73/864.81 |
| 6,315,957 | B1 | | 11/2001 | Feygin et al. | |
| 6,406,670 | B1 | | 6/2002 | Earley et al. | |
| 6,423,948 | B1 | | 7/2002 | Kwasnoski et al. | |
| 6,555,792 | B1 | * | 4/2003 | Elsener et al. | 219/428 |
| 6,638,761 | B2 | | 10/2003 | Shin et al. | |
| 6,719,949 | B1 | * | 4/2004 | Barzilai et al. | 422/66 |
| 2002/0028507 | A1 | * | 3/2002 | Heimberg et al. | 435/305.3 |

FOREIGN PATENT DOCUMENTS

| | | | | |
|---|---|---|---|---|
| EP | 1088590 | A1 | * | 4/2001 |
| GB | 1 427 034 | | | 3/1976 |
| WO | WO 90/08298 | | | 7/1990 |
| WO | WO91/17239 | | * | 11/1991 |
| WO | WO97/36681 | | * | 10/1997 |
| WO | WO 98/42442 | | | 10/1998 |
| WO | WO98/43740 | A2 | * | 10/1998 |
| WO | WO 98/56506 | | | 12/1998 |
| WO | WO 99/17881 | | | 4/1999 |
| WO | WO 99/20395 | | | 4/1999 |
| WO | WO01/28684 | A2 | * | 4/2001 |

OTHER PUBLICATIONS

Translation of DE 197 39 119 A1.

Elsener et al. v. Shin et al., Patent Interference No. 105,141, "Notice Declaring Interference," Paper No. 1, dated Aug. 13, 2003.

Elsener et al. v. Shin et al., Patent Interference No. 105,141, "Interference Initial Memorandum," attached to Aug. 13, 2003 Notice Declaring Interference, Paper No. 1.

Elsener et al. v. Shin et al., Patent Interference No. 105,141, "Shin List of Intended Preliminary Motions Under 37 CFR § 1.633," dated Sep. 2003.

Elsener et al. v. Shin et al., Patent Interference No. 105,141, "Elsener List of Intended Preliminary Motions," dated Sep. 29, 2003.

Elsener et al. v. Shin et al., Patent Interference No. 105,141, "Order Setting Times," Paper No. 18, dated Oct. 2, 2003.

Elsener et al. v. Shin et al., Patent Interference No. 105,141, "Order," Paper No. 19, dated Oct. 7, 2003.

Elsener et al. v. Shin et al., Patent Interference No. 105,141, "Summary of Telephone Conference," Paper No. 22, dated Oct. 28, 2003.

Elsener et al. v. Shin et al., Patent Interference No. 105,141, "Shin Stipulation to Level of Ordinary Skill in the Art," dated Nov. 14, 2003.

Elsener et al. v. Shin et al., Patent Interference No. 105,141, "Summary of Telephone Conference," Paper No. 24, dated Nov. 18, 2003.

Elsener et al. v. Shin et al., Patent Interference No. 105,141, "Shin Revised Stipulation to Level of Ordinary Skill in the Art," dated Nov. 25, 2003.

Elsener et al. v. Shin et al., Patent Interference No. 105,141, "Senior Party Notification of Change of Ownership of the Elsener Patent and Request for Termination of the Interference Proceedings Under CFR § 1.602," dated Jun. 10, 2004.

Elsener et al. v. Shin et al., Patent Interference No. 105,141, "Judgement—Rule 602," Paper No. 40, dated Jul. 20, 2004.

Opposition to EP 1 088 590 B1 (European Patent Application No. 00 810 855.7), filed Jan. 16, 2003 at EPO on behalf of AB Applied Biosystems, An Applera Corporation.

Opposition to EP 1 088 590 B1 (European Patent Application No. 00 810 855.7), Decision on the Termination of the Opposition Proceedings, Issued Jun. 30, 2004, along with English translation.

* cited by examiner

THERMAL CYCLING DEVICE WITH MECHANISM FOR EJECTING SAMPLE WELL TRAYS

CROSS REFERENCE TO RELATED APPLICATIONS

This application is a continuation of U.S. application Ser. No. 10/199,470 filed Jul. 22, 2002 now U.S. Pat. No. 6,638,761, which is a continuation-in-part of U.S. application Ser. No. 09/496,408, filed Feb. 2, 2000, which are all incorporated herein by reference.

FIELD

The present invention relates to an apparatus and method for ejecting sample well trays from a heating apparatus for biological samples. The apparatus improves the process of removing a sample well tray from a sample block after the cover of the heating apparatus is opened.

BACKGROUND

Biological testing has become an important tool in detecting and monitoring diseases. In the biological field, thermal cycling is utilized in order to perform polymerase chain reactions (PCR) and other reactions. To amplify DNA (Deoxyribose Nucleic Acid) using the PCR process, a specifically constituted liquid reaction mixture is cycled through a PCR protocol including several different temperature incubation periods. An aspect of the PCR process is the concept of thermal cycling: alternating steps of melting DNA, annealing short primers to the resulting single strands, and extending those primers to make new copies of double-stranded DNA. During thermal cycling, it is desirable that the temperature of each of a plurality of sample wells are substantially identical. In addition, it is important that condensation is avoided on the caps or other covering for the sample wells.

A common method of inhibiting condensation on the top of the sample wells is to provide a heated platen for pressing down on the tops or caps of the sample well trays. The platen is typically included as part of a cover and is typically metal. The platen transfers heat to the caps of the sample wells, thereby inhibiting condensation. In addition, the platen presses down on the sample wells so that the sample well outer conical surfaces are pressed firmly against the mating surfaces on the sample block. This increases heat transfer to the sample wells, and assists in providing a more uniform distribution of sample well temperatures. The platen also prevents thermal leakage from the interior of the device. Examples of a system with a platen and heated cover are described in U.S. Pat. Nos. 5,475,610, 5,602,756, and 5,710,381, all of which are assigned to the assignee of the present invention, and the contents of which are all hereby incorporated by reference herein.

The sample well trays can stick inside of the sample block due to expansion of the sample well trays and due to the force imparted on the trays by the thermal cycler cover. A considerable force may be required to unstick the sample wells and tray from the sample block and remove the tray. Unfortunately, laboratory robotic systems for removing sample well trays can sometimes have difficulty generating sufficient force to remove the sample well trays from the sample block. With the increase in the popularity of laboratory automation, it is particularly desirable to make the thermal cyclers more compatible to robotic removal of the sample well trays from the sample block. It is also desirable to increase the throughput of these devices.

SUMMARY

Various aspects provide a thermal cycling device for biological samples. The thermal cycling device may include a sample block, an annular plate, and a plurality of spring devices interposed between the sample block and the annular plate. The sample block may have a plurality of openings for receiving sample wells of a sample well tray. The sample block may further have an upper surface positioned about the outer periphery of the sample block in a region outside of the openings in the sample block. The upper surface of the sample block defines a plurality of recesses. The annular plate may be positioned adjacent the outer periphery of the sample block and be configured to abut a bottom surface of the sample well tray when the sample well tray is positioned thereon. The plurality of spring device may be interposed between the sample block and the annular plate to urge the annular plate and sample well tray away from the sample block. The spring devices may be positioned at least partially within the plurality of recesses in the sample block.

Various aspects comprise a system for ejecting a sample well tray having a plurality of sample wells configured for containing biological material from a sample block of a thermal cycling device. The sample block can be configured to be engageable with a sample well tray and comprises a plurality of openings for receiving sample wells of a sample well tray therein. The urging mechanism may be interposed between the base and the sample tray to urge the sample tray away from the sample block. The urging mechanism may comprise an annular urging plate configured to engage a sample well tray, and a plurality of springs interposed between the sample block and the annular plate to urge the annular plate away from the sample block. The plurality of springs may be positioned at least partially within a plurality of recesses in the sample block. The urging mechanism may further be configured to eject the sample wells of the sample well tray from contacting the plurality of openings of the sample block automatically upon the opening of a cover of the thermal cycling device.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate several non-limiting exemplary embodiments and together with the description, serve to explain various principles of the present teachings. In the drawings.

DESCRIPTION

Figure 1:
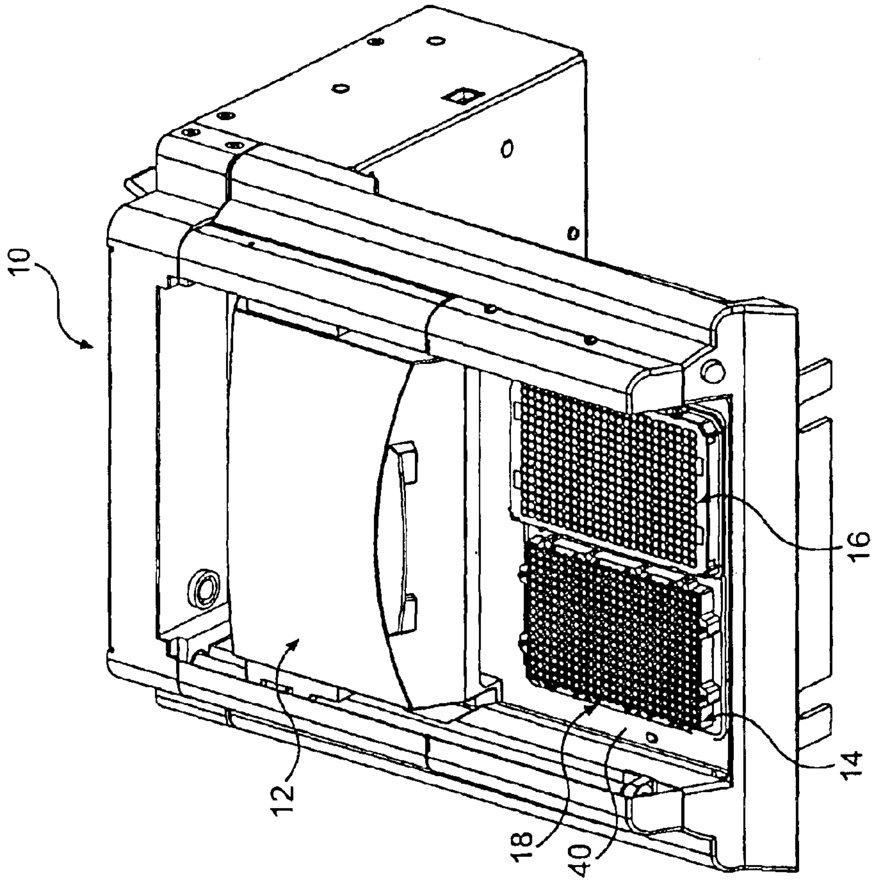
FIG. 1 is a perspective view of a thermal cycler system according to the present teachings, with a cover in an open position.

Reference will now be made to certain exemplary embodiments, examples of which are illustrated in the accompanying drawings. Wherever possible, the same reference numbers will be used throughout the drawings to refer to the same or like parts.

In accordance with the present teachings, a heating apparatus for biological samples is provided. In various embodiments, the apparatus includes a heated cover, a sample block having a plurality of openings, a sample well tray or plate having a plurality of sample wells, and an urging mechanism positioned between the sample block and the sample well tray to urge the sample well tray away from the sample block when the heated cover is moved from a closed position to an open position. As embodied herein and shown in FIGS. 1–10, the heating apparatus 10 for biological samples can include a heated cover 12, a sample block 14, a sample well tray 16, and an urging mechanism 18.

The heating apparatus 10 may be any type of conventional heating device for thermally heating biological samples. In the embodiment shown in FIGS. 1–10, the heating apparatus is a thermal cycler. The structure described below is suitable for incorporation into a number of different types of thermal cyclers, including, but not limited to, a dual 384-well Applied Biosystems 9700 thermal cycler system sold by Applied Biosystems. The thermal cycler 10 shown in the first embodiment uses two 384-well sample well trays 16, however, any other common configuration, such as a single 384-well configuration, a dual 96-well configuration, a single 96-well configuration, or a 60-well configuration can be utilized. Other configurations with any number of sample wells ranging from one sample well to several thousand sample wells may also be utilized. The present teachings are suitable for any type of heating apparatus in which sample wells are pressed into a sample block by a cover. The present teachings are suitable for use in a heating apparatus with a heated cover.

Although the description and Figures discuss trays with sample wells, the present teachings are suitable for use with sample trays that do not include wells. These trays may have a flat surface on which a sample of biological material is placed. The flat surface on which the sample is placed may be similar to a microscope slide for a sample. In this type of sample tray, a liquid may be dropped onto the tray at a plurality of positions, and then a film or cover positioned on the top surface of the tray over the samples. Alternately, a sample tray may include a porous material such a frit on the top surface, instead of sample wells, for holding samples of biological material. Therefore, although the description refers to sample well trays throughout, it should be understood that the present invention is also suitable for sample trays that do not have sample wells.

The heating apparatus may include a heated cover. As embodied herein and shown in FIGS. 1–10, the heated cover 12 is located above the sample block 14 and sample well tray 16. The heated cover is operable between an open position, as shown in FIG. 1, and a closed position where the heated cover is placed over the sample block and sample well tray. The heated cover is maintained in an open position during insertion of the sample well tray into the sample block, and is then closed during operation of the heating apparatus, i.e., thermal cycling. In the open position, the heated cover does not engage the top of the sample well tray 16. In a closed position, the heated cover 12 presses down on the top portion of the sample well tray 16, thereby providing a downward force on the sample well tray.

The top portion of each sample well of sample well tray 16 is typically defined by a cap, adhesive film, heat seal, or gap pad. In one embodiment of the present invention, a gap pad (not shown) is provided between a platen of the heated cover and the top surface of the sample well tray. The gap pad improves the distribution of the downward force on the top of the sample wells. In one embodiment, the gap pad is a MJ Research "Microseal P Type" silicon rubber plate. The gap pad will typically adhere to the platen. The gap pad may be used by itself, or in conjunction with an adhesive film or heat-sealed film. The type of cover for the sample well depends on the specific application and is not important for the purpose of the present invention. Alternately, the gap pad may be used in conjunction with caps on the top portion of the sample wells. The caps may be connected in strips, or may be individually provided as separate, unconnected caps for each sample well. Alternately, caps may be used without the gap pad. Because all of these methods can be referred to as "capping" the sample wells, the remainder of the specification will refer to the structure immediately over the sample wells as a cap, regardless of whether it is a film, pad, or cap. The basic concepts of the invention are equally applicable on each of these arrangements.

In various aspects, the heated cover may reduces heat transfer from the liquid sample by evaporation. The heated cover may also reduce the likelihood of cross contamination by keeping the insides of the caps dry, thereby preventing aerosol formation when the wells are uncapped. The heated cover may maintain the caps above the condensation temperature of the various components of the liquid sample to prevent condensation and volume loss of the liquid sample.

The heated cover may be of any of the conventional types known in the art. For example, in one embodiment, the heated cover is physically actuated to and from a closed position by a motor. In another typical embodiment, the heated cover is slid into and out of a closed position by manual physical actuation. The heated cover typically includes at least one heated platen (not shown) for pressing against the top surface of the sample well trays. Details of the heated covers and platens are well known in the art, and are described for example in U.S. Pat. Nos. 5,475,610, 5,602,756, and 5,710,381, all of which are assigned to the assignee of the present invention, and the contents of which are all hereby incorporated by reference herein. While the present teachings are described for use with a heated cover, the present teachings also perform suitably with a cover which is not heated.

In accordance with various embodiments, the heating apparatus includes at least one sample block and corresponding sample well tray. As embodied herein and shown in FIGS. 1–10, in one embodiment, the sample block 14 includes a plurality of openings 20 in a top portion thereof for receiving sample wells of the sample well tray. In the embodiment shown, each of the sample block openings may have a conical shape which is sized to fit with a sample well of a sample well tray. The sample block openings may be other shapes such as cylindrical or hemispherical, depending on the shape of the mating sample wells. Sample blocks are well known in the art. Sample blocks may be a variety of materials, e.g., metals such as aluminum or aluminum alloy. The sample block is typically machined out of a solid block of material, however casting and other techniques are also well known. It is desirable that the sample block exhibits a substantially uniform temperature across the sample well openings 20, and that the openings maintain close tolerances with the sample wells that are inserted therein.

Figure 5:
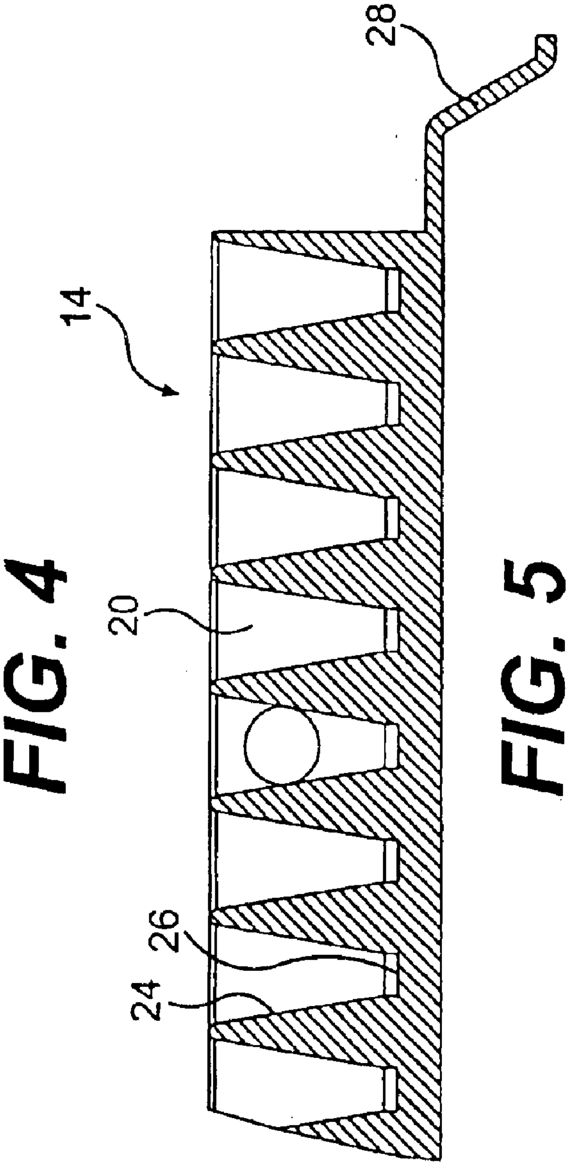
FIG. 5 is a sectional view of the sample block along line V—V of FIG. 3.
Figure 6:
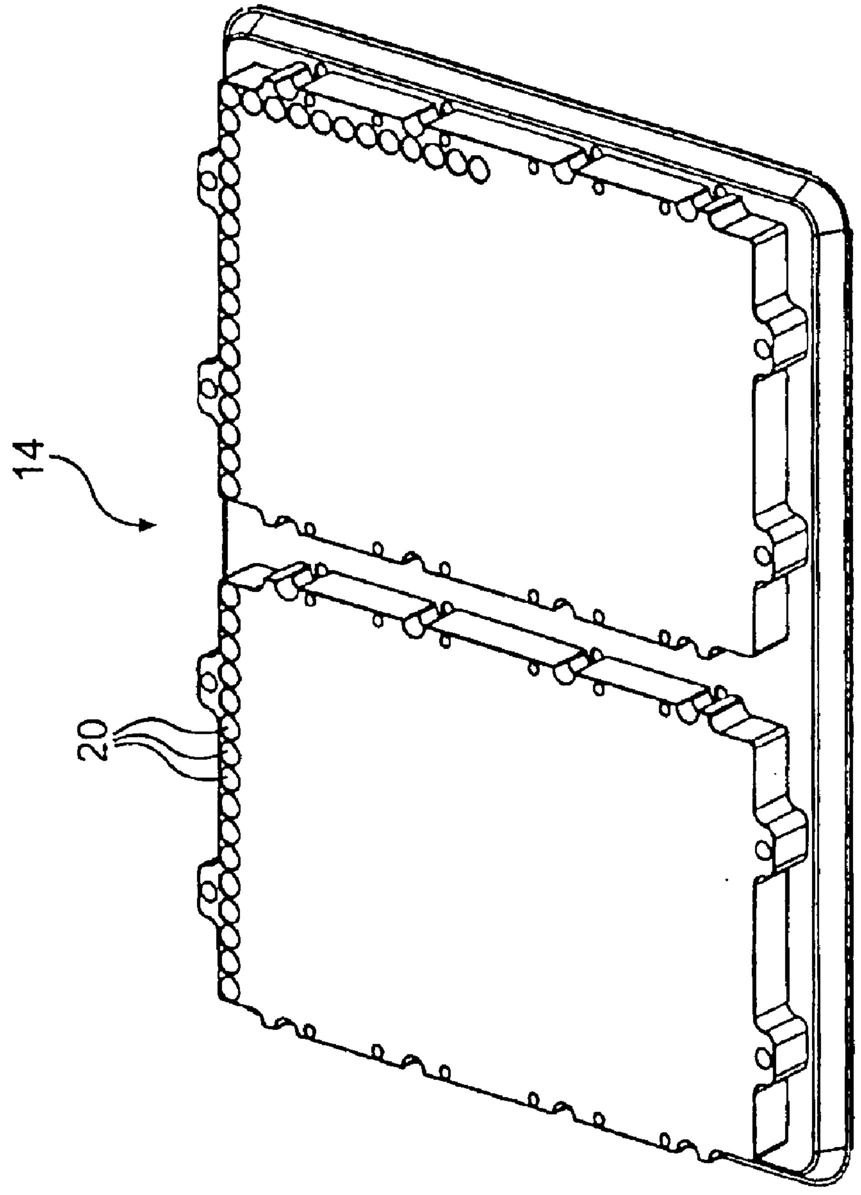
FIG. 6 is a perspective view of the sample block of FIG. 3.
Figure 7:
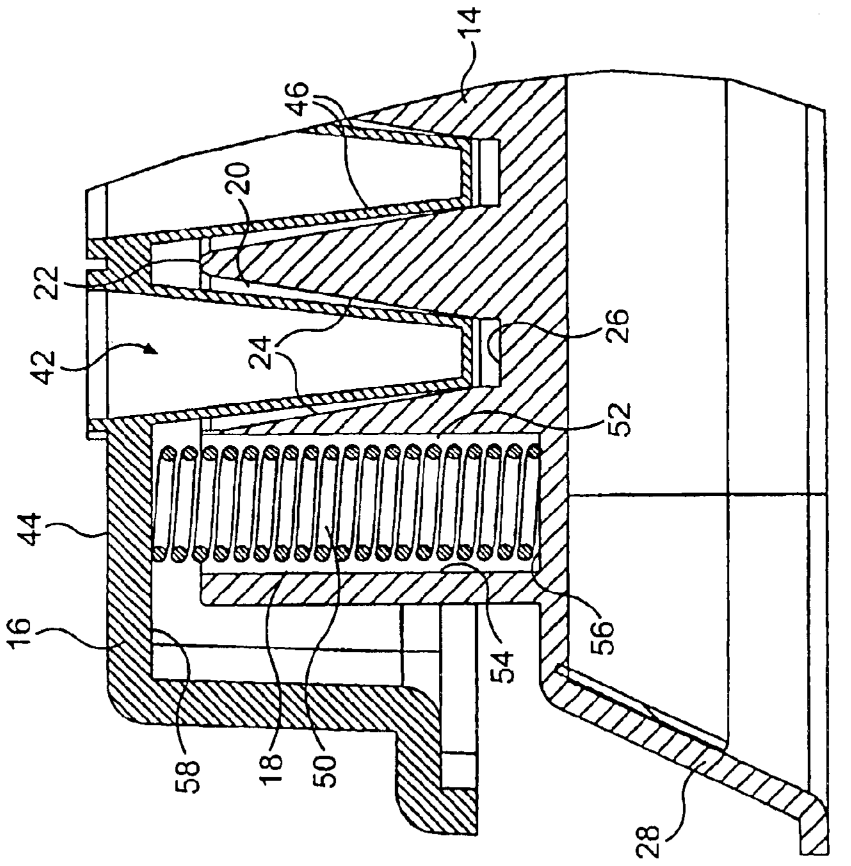
FIG. 7 is a sectional view of the sample well tray and sample block along line VII—VII of FIG. 2.
Figure 8:
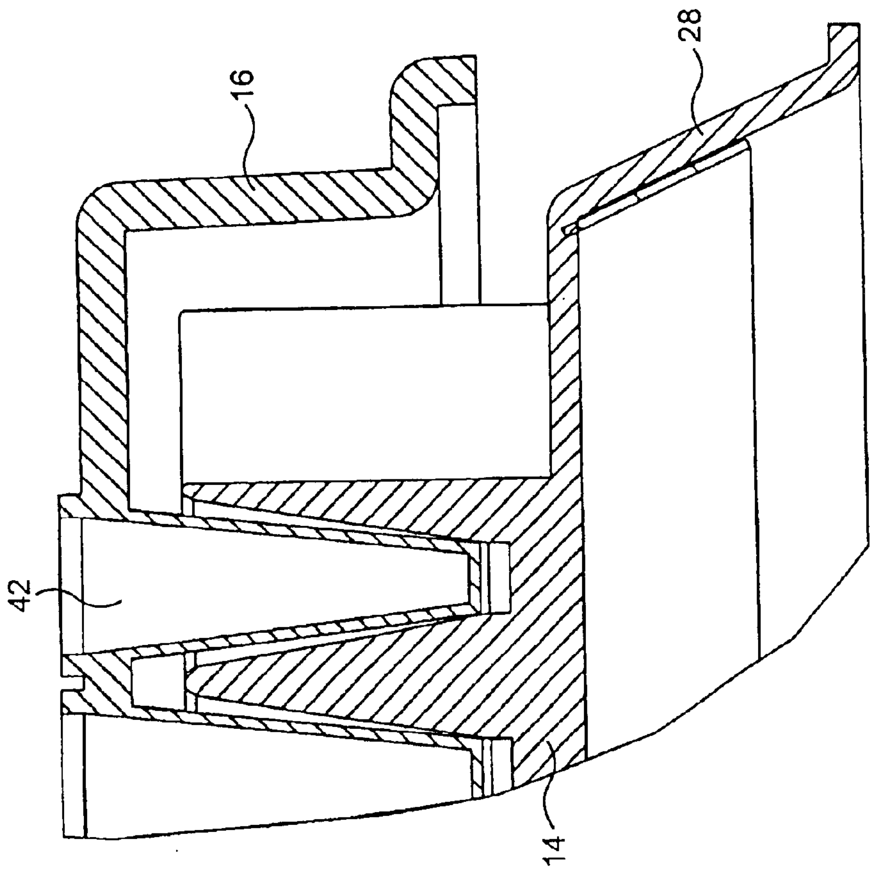
FIG. 8 is a sectional view of the sample well tray and sample block along line VIII—VIII of FIG. 2.
Figure 9B:
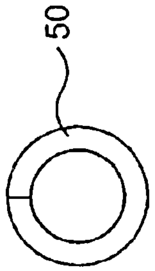
FIGS. 9A, 9B, and 9C are a side view, a top view, and a perspective view, respectively, of an ejection spring for the thermal cycler of FIG. 1.
Figure 9A:
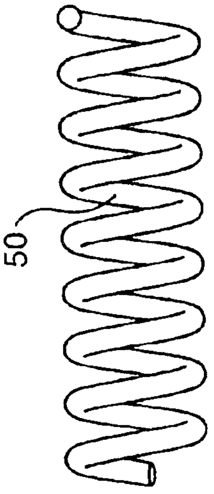
Figure 9C:
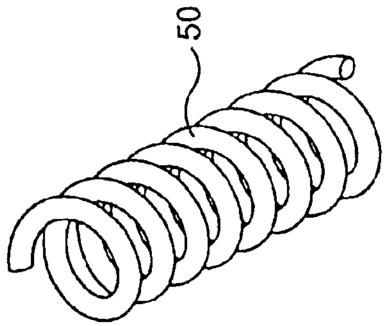
Figure 10A:
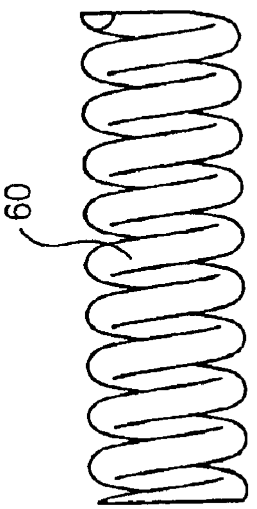
FIGS. 10A, 10B, and 10C are a side view, a top view, and a perspective view, respectively, of a second ejection spring for the thermal cycler of FIG. 1.
Figure 10B:
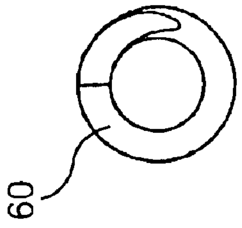
Figure 10C:
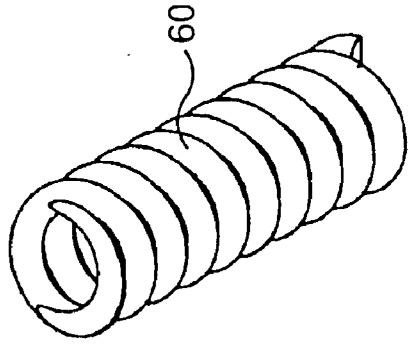

The sample blocks shown in the embodiment of FIGS. 1–10 have 384 openings arranged in a 16×24 array, however, any number of openings may be provided. Other common configurations include 96 and 60-well sample blocks, although the present invention is suitable for sample well trays having anywhere from one sample well to several thousand sample wells. Sample block openings 20 are positioned in a grid-like fashion on a top surface 22 of the sample block 14. The openings 20 are defined by a conical side wall 24 and a bottom wall surface 26 as best shown in FIGS. 5 and 7. The conical side wall 24 may slant at any appropriate angle known in the art. The size and shape of the openings shown in the drawings is by way of example only. Other designs having a different arrangement of sample wells are equally suitable with the present invention.

Sample block 14, as shown in FIG. 7, may include a bottom flange portion 28 for resting on the base 40 of the heating apparatus or any other alternate design. In one exemplary apparatus, a compression seal (not shown) may be provided between the flange portion 28 and base 40. The sample block of the present invention further includes the provision of portions engageable with an urging mechanism of the present invention. The engageable portions of the sample block will be described in greater detail later in the specification.

As embodied herein and shown in FIGS. 1–10, in one embodiment, the sample well tray 16 includes a plurality of sample wells 42 in a top surface 44 thereof, as best shown in FIG. 7. Sample well trays suitable for the present invention are well known in the art, and are also referred to as sample well plates. The present invention is flexible so that virtually any type of sample well tray may be utilized. The sample wells 42 shown in the Figures are of a conventional conical design known in the art. The sample wells may be of a variety of other shapes such as cylindrical or hemispherical.

Each sample well 42 can hold a predefined volume of liquid sample. In one embodiment of the present invention, each sample well has a total volume of approximately 30 μl and a working volume of approximately 20 μl. In the example shown in FIGS. 1–10, the sample wells have a diameter of approximately 2.20 mm and a depth of approximately 8.0 mm. The volume and dimensions of the wells can be varied depending on the specific application, as well as depending upon the number of sample wells for the sample well tray. For example, a 384-well sample well tray will typically have a smaller sample well volume than a 96-well sample well tray. The sample well tray may be made out of any of the conventional materials such as polypropylene that are typically used in sample well trays that will undergo thermal cycling of biological samples. Although the Figures illustrate the sample wells being integrally formed as part of the sample well tray, the present invention is also suitable with a sample tray where the wells are individual tubes that may be individually detached from the tray. Alternately, the tubes may be connected together in sets of rows or columns.

The sample wells 42 are designed to closely mate with the conical side walls 24 of the sample block, particularly after the heated cover applies a downward force on the sample well tray. FIG. 7 shows the spacing between sample well tube walls 46 and the sample block side walls 24 in exaggerated form for illustration purposes only. Upon closing the cover so that the platen of the cover presses onto the caps on the top of the sample well tray, any gaps between the sample well walls 46 and the sample block side walls 24 should be greatly reduced or eliminated altogether. The close mating of the sample wells in the sample block openings 20 after closing the cover improves the heat transfer rate between the sample block 14 and the sample well tray 16. Because the sample well tray is typically made of a plastic material that is slightly deformable, the sample wells of the sample well tray will also slightly deform to match the shape of the sample block openings 20. This ensures that the sample wells of the sample well tray will closely fit against the sample block to enhance the temperature uniformity of the sample wells of the sample well tray.

However, when the sample well tray 16 is urged downward by the heated cover 12, the sample well tube walls 46 impart a force on the inside surface of the sample block side walls 24. Even after the heated cover is opened so that the platen is no longer pressed against the sample well tray, the sample wells 42 of the sample well tray have a tendency to stick inside of the sample block openings 20. A significant force may be required to loosen the sample well tray 16 from the sample block 14.

In the typical prior art arrangement utilizing manual removal of the sample well tray from the sample block, an operator may need to use additional tools and significant effort to unstick the sample well tray from the sample block after the thermal cycling operation is completed. In order to loosen the sample well tray from the sample block, an operator typically grasps the sides of the sample well and imparts a rocking motion on the sample well tray while also pulling upward. The operation of manually loosening the sample wells from the sample well block openings may take up valuable time, thereby decreasing the throughput and effectiveness of the thermal cycling operation and increasing the amount of time for each sample. If the sample well trays are being robotically removed, instead of manually removed in a typical prior art arrangement, the consequences of the sticking between the sample well tray and the sample block may be even more dramatic. Robots used for sample well tray removal typically only generate very weak linear forces. Robots typically are unable to impart the rocking motion which is helpful in removing the sample well trays from the sample block openings. Because the robots are typically limited to linear motions, instead of rotational motion, a much higher force is required in order to loosen the sample well tray from the sample block. The linear robot-generated forces are frequently inadequate to overcome the initial sticking force, therefore, the sample well tray may remain stuck in the sample block. Therefore, an operator may need to loosen the sample well tray from the sample block by manually prying the sample well tray from the sample block. Alternately, robots may be designed which are capable of imparting a rotational force on the sample well trays, however, these robots will typically be larger, slower, more complex, and more expensive than existing robots.

In order to overcome these drawbacks, an urging mechanism for urging the sample well tray away from the sample block is provided. The urging mechanism tends to overcome the initial sticking force of the sample well tray in the sample block so that the sample well tray is loosened from the sample block without substantial manual or robotic assistance. The provision of the urging mechanism reduces the need for an operator to help unstick the sample well tray from the sample block, saving time, and reducing costs. Additionally, the robots used for automated handling do not need to be made unnecessarily more powerful and bulky, thereby saving cost and space. The urging mechanism may have a variety of designs, one of which is shown in the embodiment of FIGS. 1–10.

Figure 2:
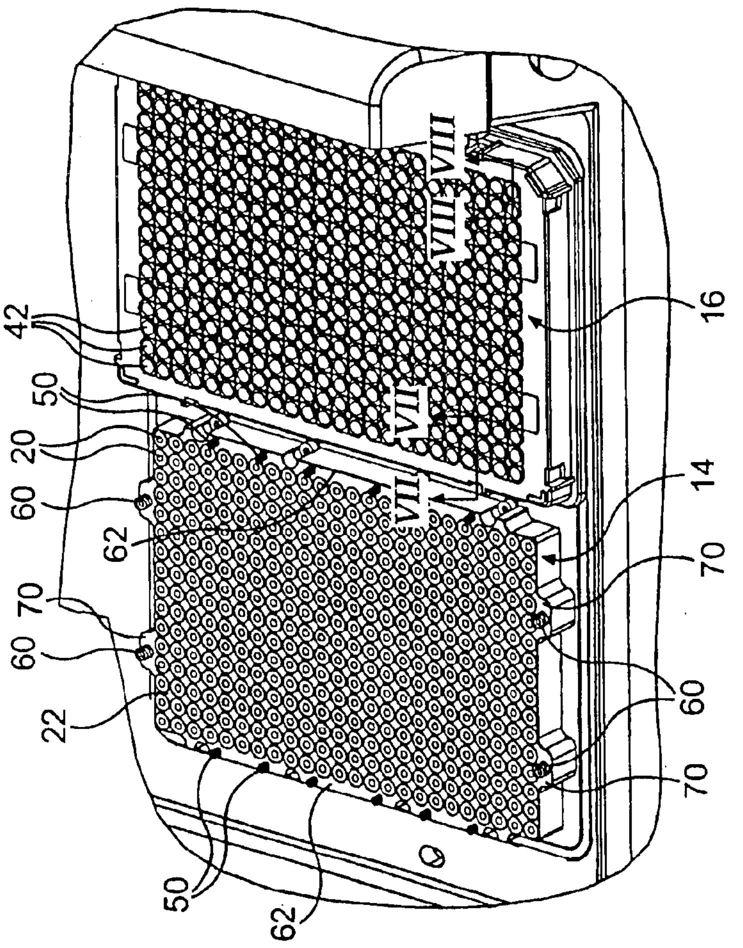
FIG. 2 is a close-up perspective view of a sample block and sample well tray of the system of FIG. 1.
Figure 3:
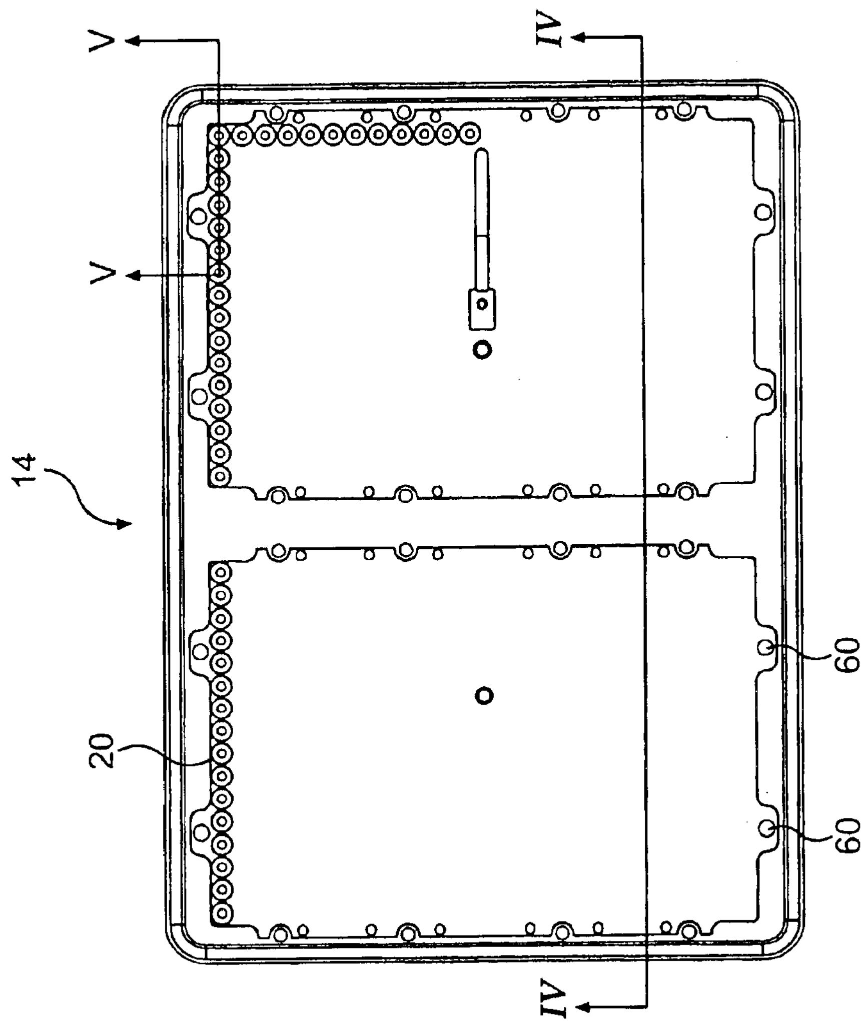
FIG. 3 is a partial top view of the sample block of FIG. 2 with the sample well tray removed.
Figure 4:
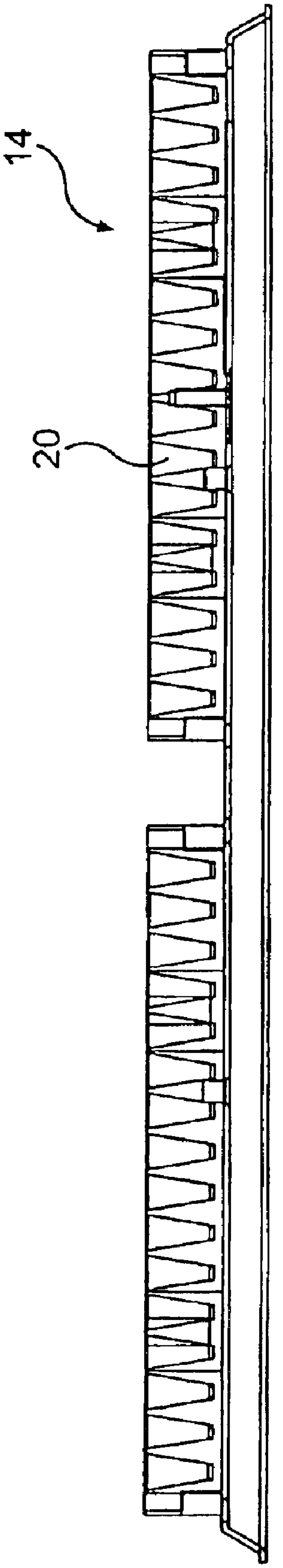
FIG. 4 is a sectional view of the sample block along line IV—IV of FIG. 3.

In one embodiment shown in FIGS. 1–10, the present teachings include urging mechanism 18 positioned between the sample block 14 and the sample well tray 16 to urge the sample well tray away from the sample block when the heated cover is moved from the closed position to an open position. In the embodiment shown in FIGS. 1–10, the urging mechanism comprises a plurality of first springs 50 and a plurality of second springs 60, as best shown in FIG. 2. The urging mechanism shown in FIGS. 1–10 is by way of example only. The urging mechanism of the present invention is not limited to the example shown in the Figures.

As embodied herein and best shown in FIG. 7, the first springs 50 are positioned in a cylindrical spring opening 52 of the sample block in one embodiment of the present invention. The cylindrical opening 52 is defined by the side surfaces 54 and end surface 56 of the cylindrical opening, as best shown in FIG. 7. Alternately, the springs may be positioned on the top surface of the sample block without the provision of a cylindrical opening, depending on the amount of unsupported spring length.

Although the urging mechanism shown in FIG. 7 is a helical compression spring, a variety of other types of urging mechanisms may be utilized. For example, a variety of other types of springs such as leaf springs, conical helical springs, and other springs which will import an axial force when compressed are suitable with the present invention. In addition, other spring-like devices suitable for use include, for example, elastomeric spring members, air cylinders, fluid cylinders, dampeners, belleville washers, and electrical solenoids. Any other suitable device that may be interposed in the system for imparting an upward force on the sample well tray may be used. The urging mechanism merely needs to be designed so that it creates sufficient force to overcome the sticking force between the sample well tray and the sample block upon opening of the cover. The urging mechanism should loosen the sample well tray from the sample block so that the sample well tray can be easily removed either robotically or manually. If a spring is used, the size and spring constant of the spring must be selected so an adequate force is imparted by the spring on the sample well tray.

In the embodiment shown in FIGS. 1–10, one end of first spring 50 abuts against the end surface 56 of cylindrical opening 52 in the sample block 14, as best shown in FIG. 7. The opposite end of spring 50 engages the lower surface 58 of the sample well tray 16. Although the Figures show the end surface 56 and lower surface 58 as being flat, other configurations may be used in order to more securely engage the spring. For example, the end surface 56 of the cylindrical opening or the lower surface 58 of the sample well tray may include grooves to closely fit the interior and/or exterior of the spring. When the spring 50 is compressed by the sample well tray, the spring 50 will impart an upward force on the sample well tray 16.

In the embodiment shown in the Figures, a plurality of springs are provided. In FIGS. 1–10, the urging mechanism 18 includes a plurality of first springs 50 and a plurality of second springs 60. The springs are positioned around an outer peripheral surface 62 of the sample block outside of the rectangular grid of sample block openings 20, as best shown in FIG. 2. In one embodiment, six first springs 50 are positioned on each longitudinal side (defined as the side with the greater number of sample well openings, for example, the side with twenty-four sample block openings in FIG. 2) of the outer peripheral top surface 62 of the sample well block.

A set of second springs 60 are positioned on each lateral side (defined as the side with the lesser number of sample well openings, for example, the side with sixteen sample block openings in FIG. 2) of the outer peripheral top surface 62 of the sample block outside of the grid of sample block openings. In the embodiment shown in FIG. 2, the second springs 60 are positioned on projections 70 that extend outward from the rectangular array of sample block openings on each lateral side of the top surface. In the FIG. 2 embodiment, two second springs 60 are located on each lateral side of the top surface. Each second spring 60 has a projection 70 for resting thereon. The second springs are similar to the first springs, but may be greater in size. The second springs 60 are typically positioned in cylindrical openings similar to those used for the first springs 50, although the cylindrical openings may not be necessary in some arrangements. With the arrangement shown in FIGS. 1–10, a total of sixteen springs (twelve first springs and four second springs) are utilized on the outer periphery of the sample block 16. The number and specific arrangement of springs can be varied greatly depending on the specific application.

It is desirable that the urging mechanism provide a substantially uniform force on the sample well tray in order to reduce undue bending of the sample well tray. As the force is more evenly distributed, more lightweight and thinner sample well trays may be used. Therefore, costs can be reduced for the sample well tray production and materials if the urging mechanism distributes the upward force in a substantially uniform manner. If few, large force points were used, the tray may become locally deformed in a way that could affect the handling of the tray later in the process. Lastly, the application of a substantially uniform spring force around the periphery of the sample well tray may help reduce evaporation losses from locations adjacent the periphery of the sample well tray by ensuring that the sample well tray is firmly and evenly placed against the heated cover. Therefore, in one embodiment, it is preferable to provide a large number of substantially uniformly spaced springs for the urging mechanism.

Springs 50 and 60 of urging mechanism 18 provide an upward force on the sample well tray that is sufficient to overcome the sticking force caused by the cover and loosen the sample well tray from the sample block upon opening of the cover. The upward force applied by the springs should be less than the downward force applied by the cover or the cover will not remain closed. The downward force imparted by the cover is typically significantly greater than the upward force imparted by the springs in order to ensure good thermal contact between the sample wells of the sample well tray and the openings of the sample block.

An example of suitable type springs used in one embodiment of the urging mechanism is shown in FIGS. 9A–9C and 10A–10C. The springs of this embodiment, by way of example only, are helical coil springs selected to impart sufficient force to urge the sample well tray away from and slightly out of the sample block after the cover is opened. In one example of the present invention shown in FIGS. 9A–9C and 10A–10C, the first springs 50 have an outside diameter of 1.92 mm, length of 6.3 mm, and spring rate of 0.275 kg/mm. During closing of the cover, these first springs 50 each compress 1.15 mm thus imparting an ejecting force of 0.316 kg each. In the same example, the second springs 60 have an outside diameter of 3.05 mm, length of 9.53 mm, and spring rate of 0.987 kg/mm. During closing of the cover, these second springs 60 each compress 1.55 mm thus imparting an ejecting force of 1.53 kg. In the present example, there are twelve first springs and four second springs, resulting in a total spring force applied to the sample well tray of 9.91 kg. These numbers are by way of example only for one embodiment of the present invention. As is clear from the above description, a greater or lesser number of springs with different spring constants, shapes and sizes may be desirable in order to vary the upward force imparted by the urging mechanism upon opening of the cover, compared to the above example.

The particular springs used in the above example were made of stainless steel, however other suitable materials are also acceptable. The springs are preferably of a low thermal mass compared to the sample block and therefore do not materially affect the performance of the system. Therefore, the sample block and sample well tray maintain a substantially uniform temperature distribution that is not affected by the urging mechanism 18.

The operation of the heating apparatus for one typical embodiment will now be described below. First, the heated cover 12 of the thermal cycler is positioned in a first open position. A sample well tray with a predetermined amount of liquid sample in some or all of the sample wells is placed on top of the sample block. In the dual 384-well assembly shown in FIGS. 1–10, two sample well trays are provided, one for each of the sample blocks. The sample well tray 16 typically includes either an adhesive film, a heat seal film, a gap pad, or individual caps for covering each of the sample wells 42 at the time of insertion into the thermal cycler. The sample wells 42 are aligned with the sample block openings and inserted downward into the conical sample block openings 20. The heated cover is then slid so that it is placed over the sample well trays and sample block. The heated cover is then manually or automatically closed.

As the heated cover closes, a heated platen (or the gap pad located below the platen) of the heated cover 12 presses down on the top of the sample wells to firmly press the sample wells 42 into the sample block openings 20, as best shown in FIG. 7. As the heated cover closes, the first and second springs 50 and 60 of the urging mechanism 18 are compressed by a bottom flat surface 58 of the sample well tray on the outside periphery of the sample wells 42. As the springs are compressed, the compression springs impart an upward force on the sample well tray 16 while the heated cover is in its closed position. While in the closed position, the thermal cycler then thermally cycles the liquid sample in the sample well tray to undergo a PCR or other type of chemical reaction.

After the thermal cycling and/or other operations are completed, the heated cover 12 is opened (either manually or automatically). As the heated cover is opened, the platen (or gap pads) of the heated cover will no longer press against the top of the sample wells. Simultaneously, the springs of the urging mechanism 18 will impart an upward force on the bottom surface 58 of the sample well tray, thereby urging the sample wells 42 out of the sample block openings 20. The springs should impart sufficient force so that the sample well tray 16 will become loosened from the sample block 14 and be raised a slight distance in an upward direction. After the sample well tray is loosened from the sample block, the sample well tray may be robotically lifted out of and away from the sample block without any additional manual steps. As previously discussed, the provision of the urging mechanism allows the sample well tray to be more quickly and efficiently removed from the sample block.

As is clear from the above description, the present invention includes a method of assisting in the removal of a sample well tray from a sample block. The method includes the steps of providing an initial downward force on a sample well tray by closing a cover. The initial downward force presses sample wells of the sample well tray into openings on a top surface of a sample block. The method further includes the step of providing an upward force on the sample well tray by a spring system positioned between the sample well tray and the sample block, the upward force being substantially smaller than the initial downward force. The cover is then opened to remove the initial downward force on the sample well tray, and the sample well tray is urged from the sample block by the upward force from the spring mechanism.

The system and method according to the present teachings reduce the amount of time that it takes to remove the sample well tray from the sample block. The urging mechanism arrangement allows the sample well tray to be automatically removed from the sample well block without unduly exposing an operator to the chemicals in the sample well tray which may occur during manual handling of sample well trays. The system and method according to the present teachings are not limited by the examples shown above which are for purposes of illustration only.

In another aspect, the present teachings includes a heating apparatus of a second embodiment. In this embodiment, the apparatus includes a heated cover, a sample block having a plurality of openings, a sample well tray having a plurality of sample wells, a sample well tray holder for supporting the sample well tray, and an urging mechanism positioned between the sample block and the sample well tray holder to urge the sample well tray away from the sample block when the heated cover is moved from a closed position to an open position. As embodied herein and shown in FIGS. 11–13, the heating apparatus 100 for biological samples includes a heated cover 110, a sample block 112, a sample well tray 114, a sample well tray holder 116, and an urging mechanism 118.

Figure 11:
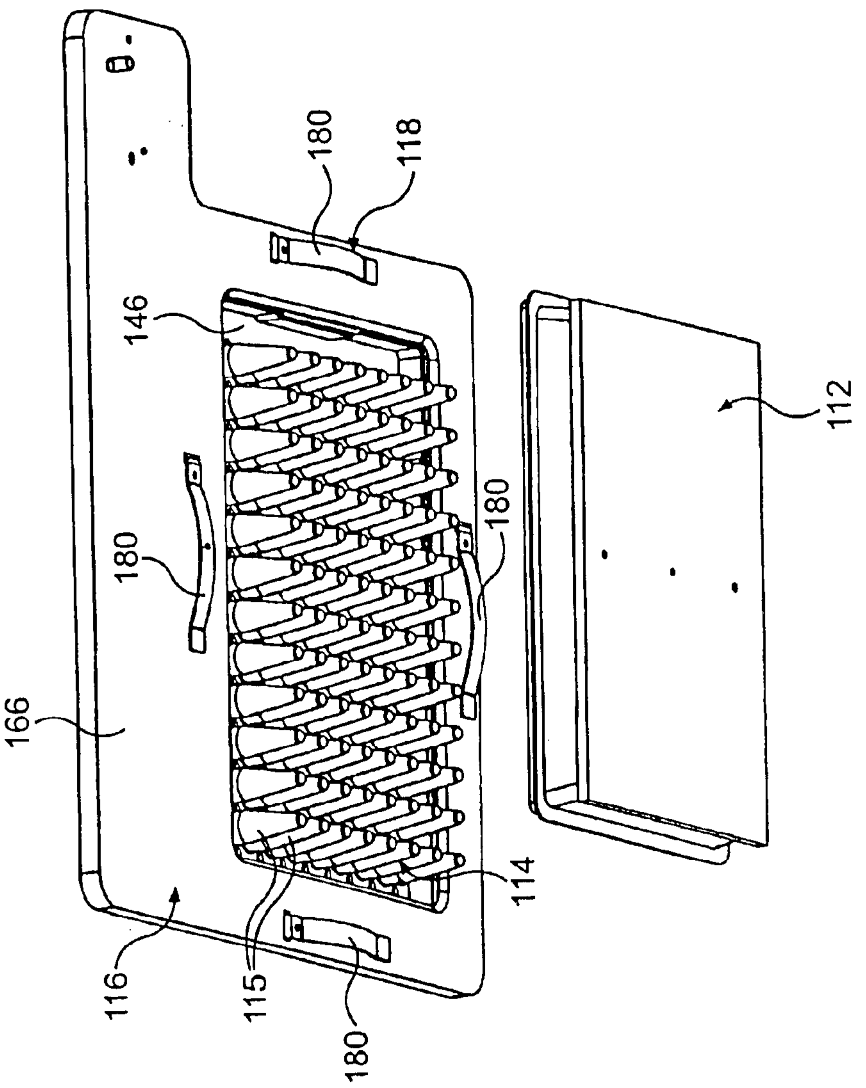
FIG. 11 is a perspective view of a sample well tray, sample well tray holder, and sample block according to a second embodiment of the present teachings.
Figure 12:
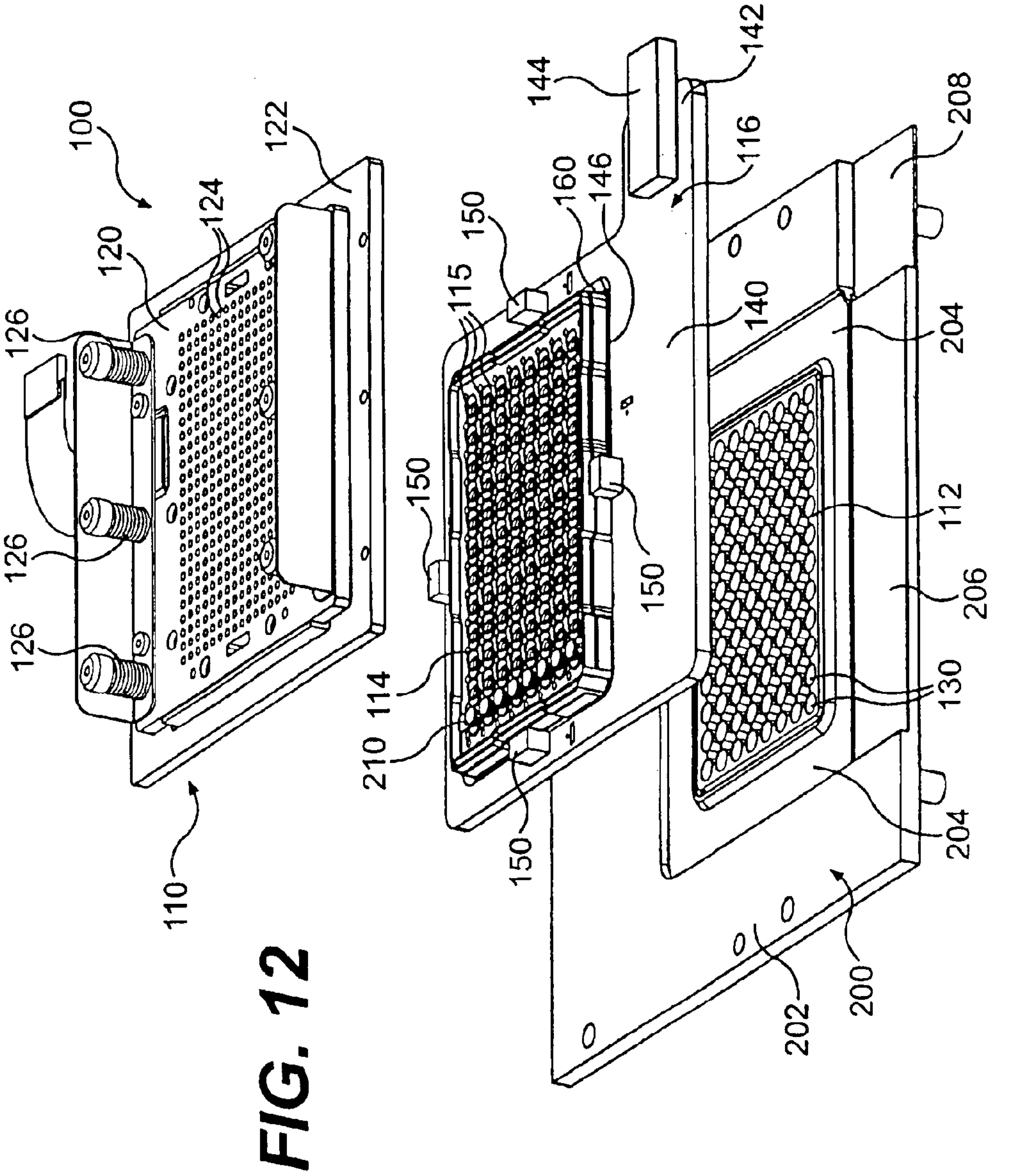
FIG. 12 is a perspective view of the apparatus of FIG. 11 including a cover and a base.

The heating apparatus of the embodiment shown in FIGS. 11–13 is suitable for use in a variety of thermal cycler systems, including, but not limited to, a 96-well Applied Biosystems thermal cycler with optical detection capability. The heating apparatus is also suitable for other types of thermal cyclers with different numbers of wells, as well as those without optical detection capabilities. The present teachings are suitable for a heating apparatus in which sample wells are pressed into a sample block by a cover. Similar to the first embodiment, the present teachings are suitable for use in a heating apparatus with a heated cover.

The heating apparatus may include a heated cover. As embodied herein and shown in FIGS. 11–13, the heated cover 110 is located above the sample block 112, sample well tray 114, and sample well tray holder 116. The heated cover is operable between an open position in which the heated cover does not impart a downward force on the sample well tray, and a closed position where the heated cover imparts a downward force on the sample well tray.

In an exemplary embodiment shown in FIGS. 11–13, the heated cover 110 includes a central cover portion 120 and an outside cover portion 122. In the embodiment shown in FIG. 12, the central cover portion 120 has a plurality of openings 124 for the optical detection of reactions that occur in the sample wells of the sample well tray. The present teachings are also suitable for use in a thermal cycler without optical detection capabilities. In one embodiment shown in FIGS. 11–13, the outside cover portion 122 is movable in an upward and downward direction relative to the central cover portion 124. The movement of the outside cover portion 122 relative to the central cover portion 124 assists in isolating the spring force of an urging mechanism from the sample well tray during thermal cycling protocols.

The heated cover 110 of FIGS. 11–13 also includes a plurality of distribution springs 126 for distributing the force of the central cover portion 120 onto the sample well tray 114. The distribution springs 126 also allow for the upward and downward motion of the outside cover portion 122 relative to the central cover portion 120. Each distribution spring 126 includes a pin (not shown) positioned inside of the helical spring. The pin passes through the central cover portion 120 and is connected to the outside cover portion 122 so that the central cover portion and outside cover portion are biased toward one another. A driving mechanism (not shown) drives the central cover portion 124 and outside cover portion 122 in a downward direction so that the heated cover presses firmly on the sample well tray in a manner which will be described in greater detail below.

The heating apparatus may also include a sample well tray and sample well tray holder for supporting the sample well tray. As embodied herein and shown in FIGS. 11–13, the sample well tray 114 may be a conventional sample well tray known in the art with a plurality of sample wells 115. In the embodiment shown in FIGS. 11–13, the sample well tray is a 96-well tray, however the instant invention is applicable for use with sample well trays having any number of wells from one or two wells to several thousand. For example, the present teachings are also suitable for use with 384 and 60-well trays known in the art. The present teachings are suitable for use with sample well trays having a variety of sizes and shapes. In the example shown in FIGS. 11–13, the sample wells have a working volume of 200 μl, a diameter of 5.50 mm and a depth of 20.0 mm. The volume of the sample wells may vary anywhere from 0.1 μl to thousands of microliters (μl), with a volume between 50 to 500 μl being typical, with a volume of 100 to 200 μl being most preferred. Similar to the embodiment of FIGS. 1–10, the heating apparatus of FIGS. 11–13 is also suitable for use with sample trays where the liquid sample is placed on a structure other than a sample well, such as a microscope slide or a frit.

In contrast to the embodiment of FIGS. 1–10, the heating apparatus of FIGS. 11–13 further includes a sample well tray holder 116 for supporting the sample well tray. The sample well tray holder 116 is in the shape of a flat plate with a main body portion 140 and an arm portion 142. In the example shown in the drawings, the main body portion 140 is in a rectangular shape. The main body portion 140 also defines a rectangular opening 146 for the sample well tray 114. The sample well tray holder is preferably made out of a material with poor heat conduction characteristics and a low thermal mass. In one embodiment, the material selected for the sample well tray holder is a polycarbonate. Other suitable materials are also acceptable.

In one embodiment, the arm portion 142 of the sample well tray holder 116 projects on the same plane as the main body portion 140, and is used for connection to a robotic manipulator (not shown). A robotic manipulator may grasp the arm portion 142 via the clamping mechanism 144 positioned on the end of the arm portion 142 and swing the main body portion into position to insert the sample well tray 114 into the heating apparatus. The robotic manipulator also allows for the sample well tray to be moved upward and downward over the sample block, and preferably initiates an additional downward movement on the sample tray holder to isolate the sample well tray from the urging mechanism when the cover is in its closed position, as will be described in greater detail.

The main body portion 140 of the sample well tray holder may include a plurality of bosses 150 projecting upward from the top surface thereof. The bosses shown in the Figures are for purposes of illustration only, as the bosses can be of any variety of sizes, shapes, and designs. For example, the bosses could also be a ridge around the outside periphery of the opening for the sample well tray. The bosses could also be significantly lengthened compared to those shown in FIG. 12. The function of the bosses will be described in greater detail below.

Figure 13A:
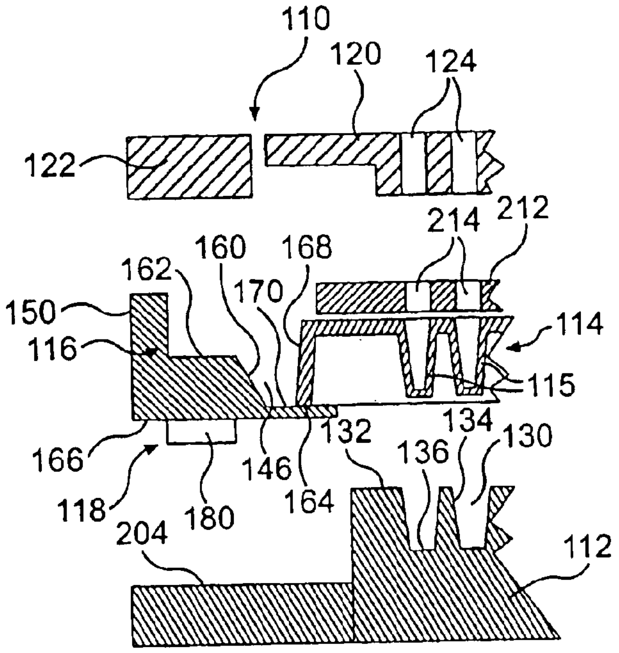
FIG. 13 is a schematic illustrating the operation of the apparatus of FIGS. 11–12.
Figure 13B:
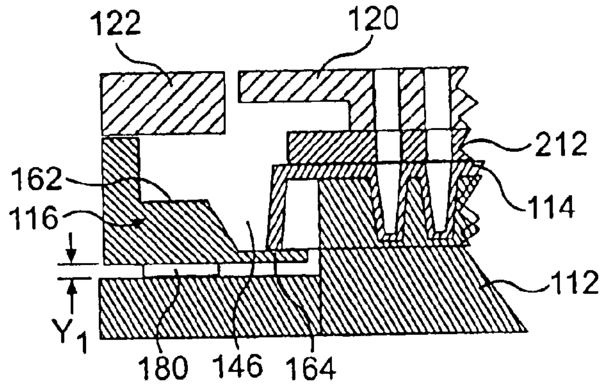
Figure 13C:
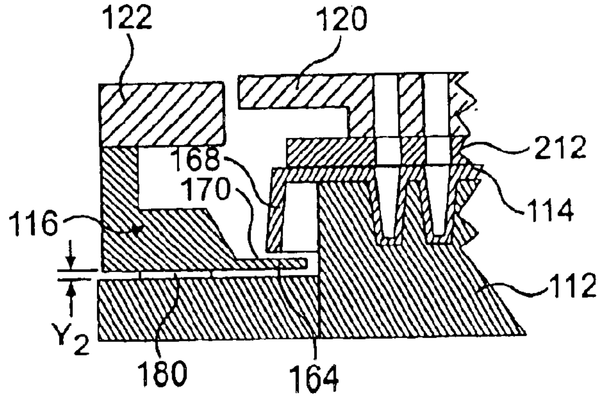

The rectangular opening 146 of the sample well tray holder is designed so that the sample well tray 114 may rest on the sample well tray holder 116. This is shown for example in the schematic of FIGS. 13A–13C. The rectangular opening 146 is defined by a tapered wall 160 which tapers downward from the top surface 162 of the sample well tray holder 116. The opening defined by the tapered wall 160 is greater in length and width than the length and width of the sample well tray 114. The tapered wall 160 tapers until it meets a floor portion 164 which extends from the tapered wall 160. The floor portion 164 extends along the bottom surface 166 of the sample well tray holder. The floor portion 164 defines a rectangular opening that is smaller than the size of the sample well tray. When the sample well tray is placed in the rectangular opening 146, outer side walls 168 of the sample well tray rest on a top surface 170 of the floor portion. This is best shown in the schematic of FIGS. 13A–13C. When the sample well tray 114 is placed in the rectangular opening 146 so that the sample well tray rests on the floor portion 164, the sample well tray 114 is free to move in an upward direction relative to the sample well tray holder 116. In the embodiment shown schematically in FIGS. 13A–13C, the floor portion 164 is thinner than the remainder of the sample well tray holder 116. The sample well tray holder of FIGS. 11–13 is shown for purposes of illustration only.

The heating apparatus includes a sample block including a plurality of openings for the sample wells of the sample well tray. As embodied herein and shown in FIGS. 11–13, the sample block 112 includes a plurality of sample block openings 130 in a top surface 132 of the sample block. The openings are defined by conical side walls 134 similar to those described for FIGS. 1–10 and a bottom surface 136. The sample block 112 is positioned in a base 200 for supporting the sample block. As best shown in FIG. 12, base 200 includes a raised surface 202, a first lower surface 204, a second lowered surface 206, and third lowered surface 208. The first lowered surface 204 is sized to accommodate the main body portion 140 of the sample well tray holder 116. Additionally, the first lowered surface 204 defines a recess for receiving the sample block 112 therein. The second and third lowered surfaces, 206 and 208, are sized to also accommodate the sample well tray holder. The first lowered surface 204 of the base is configured to engage the urging mechanism as will be described below.

In accordance with the present teachings, the heating apparatus includes an urging mechanism for urging the sample well tray out of the sample well block upon opening of the cover. As embodied herein and shown in FIGS. 11–13, the urging mechanism 118 may include any suitable type of mechanism such as a spring device for pressing upward on the sample well tray holder and sample well tray when the heated cover is opened. In one embodiment, the urging mechanism 118 includes a plurality of springs. More particularly, the plurality of springs comprise leaf springs 180 attached to a bottom surface 166 of the sample well tray holder 116. The leaf springs, in one embodiment, are attached to the bottom surface 166 of the sample well tray holder. Alternately, the leaf springs could be attached to the sample well block. In the particular embodiment shown in FIGS. 11–13, the leaf springs 180 were attached to the sample well tray holder, instead of the sample block, in order to make cleaning of the heating apparatus more easy. Additionally, the arrangement of the leaf springs on the sample well tray reduces the thermal effect of the leaf springs on the sample block, compared to if the leaf springs were attached to the sample block.

In the embodiment of FIG. 11, four leaf springs 180 are attached to the bottom surface 166 of the sample well tray holder 116. The four leaf springs are substantially symmetrically spaced around the sample well tray. Although, the Figures show four leaf springs, anywhere from one to several dozen leaf springs could be used with the present invention. It is desirable that the leaf spring be comprised of a non-corrosive material that will maintain reasonably constant spring characteristics. In one embodiment, the material for the leaf spring is beryllium copper. Any other suitable material is also acceptable.

The urging mechanism of the present invention is not limited to the design shown in FIGS. 11–13. The urging mechanism may also be made out of any variety of force imparting devices instead of the leaf springs shown in FIGS. 11–13 such as coil springs, hydraulic dampeners, elastomeric springs, or other conventional spring devices. Leaf springs were selected in the particular embodiment because of the large distance between the bottom surface 166 of the sample well tray 114 and the first lower surface 204 of the base 200. The use of a coil spring is possible with this configuration, however there may be a substantial amount of unsupported spring length if a coil spring is used. Therefore, types of springs besides coil springs may be desirable if the amount of unsupported spring length is substantial in the particular configuration.

The sample wells 115 of the embodiment of FIGS. 11–13 may be covered by any of the conventional methods known in the art. For example, FIG. 12 shows a row of sample well caps 210 for covering the top of the sample wells 115. The caps may be individual, or grouped in rows of eight as shown in FIG. 12. Alternatively, instead of using caps, an adhesive film can be used to seal off the sample wells. Another typical type of seal known in the art is a heat seal film. Any of these known structures may be utilized for covering the sample wells.

In addition to the sample well covering or sealing method, a thin compliant cover may be placed between the heated cover and the top of the sample well tray. This compliant cover is similar to the gap pad that may be utilized in the FIGS. 1–10 embodiment, but does not typically supply a seal to the top of the sample wells. In other embodiments, the compliant cover serves the function of the cover and gap pad. An example of a typical compliant cover is shown in FIGS. 13A–13C, as reference number 212. The compliant cover 212 helps to evenly distribute the downward force imparted by the heated cover onto the sample well tray. The compliant cover may be made out of a polymeric, composite material or other material that can withstand the high temperatures experienced during thermal cycling. The compliant cover of FIGS. 11–13 is typically used in conjunction with the sealing methods (caps, adhesive tape, etc.) for the sample wells. The compliant cover typically includes detection holes 214 aligned with each of the sample wells 115 of the sample well tray 114. The detection holes 214 are also aligned with the openings 124 on the central cover portion 120 of the heated cover for allowing light emissions from the liquid sample to be detected by a detection apparatus (not shown).

The operation of the heating apparatus for one typical embodiment corresponding to FIGS. 11–13 will now be described. First, the heated cover 12 of the thermal cycler may be positioned in a first open position. The sample well tray 114 is then placed into the sample well tray holder 116 either manually or automatically. At this time the sample wells 115 of the sample well tray have already been filled with the appropriate biological liquid samples. The sample wells have also been sealed by the appropriate method, such as placement of caps 210 on the sample wells. The sample well tray holder 116 is then rotated by the robotic manipulator so that the sample well tray holder and sample well tray are positioned between the heated cover 110 and the sample block 112 as shown in FIG. 13A.

After the sample well tray holder and sample well tray are positioned as shown in FIG. 13A, the sample well tray holder 116 and sample well tray 114 may be lowered so that the sample wells 115 are positioned inside the sample block openings 130. The sample well tray holder and sample well tray are lowered by either the robotic manipulator moving them downward or by pressing the heated cover 110 downward, depending on the particular configuration. The heated cover 110 is moved downward by either manual or automatic operation, so that the sample wells 115 of the sample well tray 114 are pressed firmly into the openings 130 of the sample block as shown in FIG. 13B.

FIG. 13B illustrates the heated cover in a closed position, which will be referred to as the “seated” position. In the seated position, the leaf springs 180 are compressed between the sample well tray holder 116 and the first lowered surface 204 of the base. In this first lowered position or seated position shown in FIG. 13B, the bottom surface 166 of the sample well tray holder 116 is spaced by the distance of y1 from the top surface 204 of the base. The top surface 170 of the floor portion 164 of the sample well tray holder is pressed against the bottom of the side wall 168 of the sample well tray by the spring force of leaf springs 180. The upward force imparted on the side wall of the sample well tray has a tendency to cause bending of the sample well tray.

The seated position shown in FIG. 13B is only obtained for a brief moment. In one method of operation, a heated cover actuator (not shown) will press downward on the outside cover portion 122 of the heated cover 110 so that the sample well tray holder 116 will move slightly downward relative to the sample well tray 114 to the position shown in FIG. 13C. In this manner, the top surface 170 of the floor portion 164 will become spaced from the bottom of the side wall 168 in order to isolate the sample well tray 114 from the spring force generated by the leaf spring 180 while in the compressed position shown in FIG. 13C. The position shown in FIG. 13C will be referred to as the compressed position, because the leaf spring is compressed even farther so that the spacing between the bottom surface 166 of the sample well tray holder 116 and the top surface 204 of the base is reduced to a measurement of y2. In the compressed position, the sample well tray holder 116 will not press upward on the side wall 168 thereby substantially preventing bending of the sample well tray 114. This reduces the amount of volume loss due to bending.

The heating apparatus may be thermally cycled upon being positioned in the compressed position of FIG. 13C. After the apparatus has been thermally cycled, the mechanism for driving the heated cover downward is released in order to open the cover. The heated cover no longer contacts the top of the sample well tray. The leaf spring 180 simultaneously pushes the sample well tray holder 116 upward. The top surface 170 of the floor portion 164 then engages the bottom of the side wall 168 of the sample well tray 114, and pushes upward on the sample well tray. The force imparted on the sample well tray is sufficient to overcome the initial sticking force, and the sample well tray is loosened from the sample block. The sample well tray 114 is thus safely ejected from the sample block 112 so that the robotic manipulator may remove the sample well tray holder and sample well tray from the sample block.

In yet another aspect, the present teachings include a thermal cycling device of a third embodiment. In this embodiment, the device includes a cover, a sample block having a plurality of openings for receiving sample wells of a sample well tray therein, an annular plate positioned above the sample block adjacent the outer periphery of the sample block, and a plurality of spring devices interposed between the sample block and the annular plate to urge the sample well tray away from the sample block when the cover is moved from a closed position to an open position. As embodied herein and shown in FIGS. 14–21, the thermal cycling device 310 includes a heated cover 312, a sample block 314, an annular urging plate 316, a plurality of spring devices 318 and 320, and a sample well tray 322.

The heating apparatus 310 shown in FIGS. 14–21 is a thermal cycler. The structure described below is suitable for incorporation into a number of different types of thermal cyclers, including, but not limited to, an Applied Biosystems 9700 thermal cycler system sold by Applied Biosystems. Whereas FIGS. 1–10 show a dual 384-well system, FIGS. 14–22 show a dual 96-well system. It should be understood that the FIGS. 14–22 embodiment is suitable with any other number of configurations, such as, but not limited to, a single or dual 384-well configuration, a single 96-well configuration, or a single or dual 60-well configuration. The FIGS. 14–22 embodiment is also suitable with other configurations with any number of sample wells ranging from one sample well to several thousand sample wells. Similar to the first two embodiments, the present teachings are suitable for use in a thermal cycling device with a heated cover, although it may also be used with a device in which the cover is not heated. The description of the thermal cycling device from FIGS. 1–10 is incorporated herein.

Figure 14:
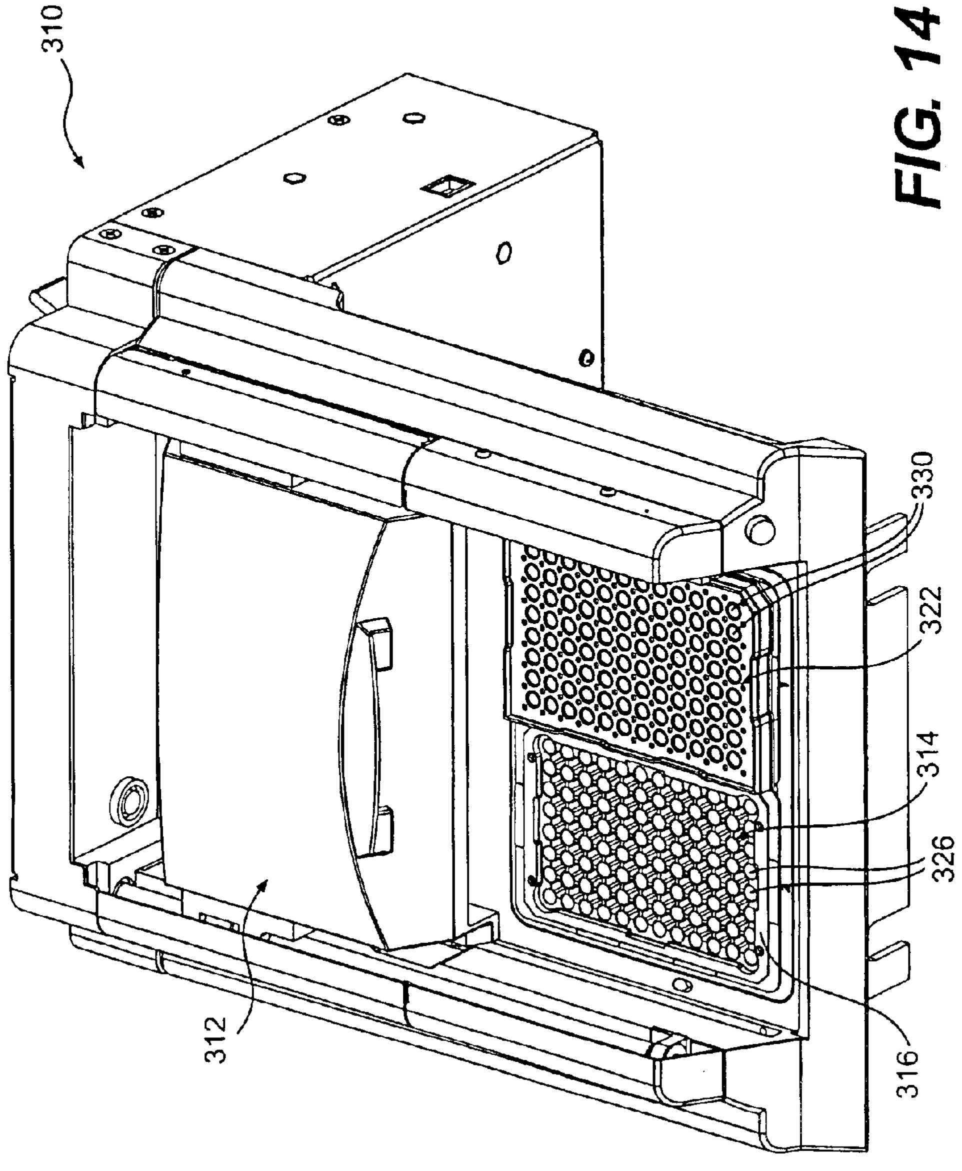
FIG. 14 is a perspective view of a thermal cycler system according to a third embodiment of the present teachings.
Figure 15:
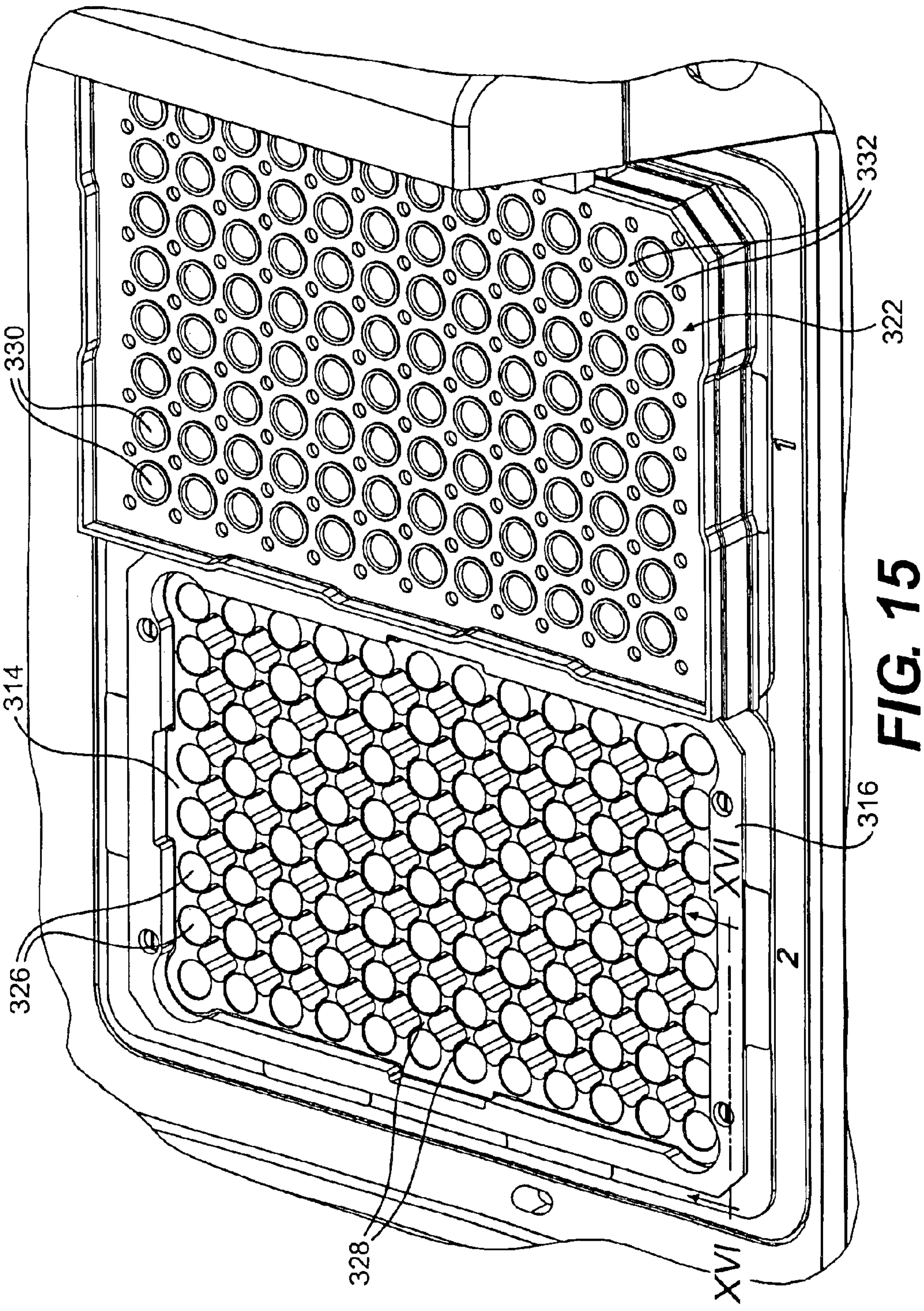
FIG. 15 is a close-up perspective view of a sample block, annular urging plate, and sample well tray of the system of FIG. 14.

To the extent that the third embodiment shows structure that has been previously described in relation to the other embodiments, such description may be omitted below. For example, the heated cover 312 roughly corresponds to the heated cover 12 in FIG. 1, except that the heated cover 312 is configured to accommodate a pair of 96-well sample trays, whereas the heated cover 12 of FIG. 1 is configured to accommodate a pair of 384-well sample trays. The heated cover 312 is operable between an open position, as shown in FIG. 14, and a closed position where the heated cover is placed over the sample block and sample well tray. In the closed position, the thermal cycling device may perform thermal cycling, while the heated cover 312 presses down on the top portion of the sample well tray 322, thereby providing a downward force on the sample well tray. The description of the function and structure of the heated cover from FIGS. 1–10 is incorporated herein.

The thermal cycling device includes at least one sample block. As embodied herein and shown in FIGS. 14–21, in one embodiment, the sample block 314 includes a plurality of openings 326 positioned in a top surface 328 thereof in a well-known manner for receiving sample wells of a sample well tray. In the embodiment shown in FIGS. 14–21, each of the sample block openings 326 has a conical shape that is sized to fit with a sample well of a sample well tray, in a manner similar to that described for FIGS. 1–10. As previously described for the sample block 14 in FIGS. 1–10, the sample block openings 326 of the sample block 314 may have a variety of sizes, shapes and materials. The sample blocks shown in the embodiment of FIGS. 14–21 have 96 openings arranged in a well-known 8×12 array, however any number of openings may be provided.

In accordance with the present teachings, the thermal cycling device may be configured for thermally cycling a plurality of biological samples contained in a sample well tray. As embodied herein and shown in FIGS. 14–21, in one embodiment, the sample well tray 322 includes a plurality of sample wells 330 in a top surface 332 thereof. In the embodiment shown in FIGS. 14–21, the sample well tray has 96 wells arranged in a 8×12 array. It should be understood that the sample well tray may have anywhere from one to at least several thousand sample wells. A variety of sample well trays suitable for the present teachings are known in the art, and may also be referred to as sample well plates. The sample wells may be of a variety of other shapes such as cylindrical or hemispherical. As described in the FIGS. 1–10 embodiment, each sample well can contain a predefined liquid sample of biological material. As can be seen, the present teachings are suitable with a large number of different configurations of sample well trays.

As in FIGS. 1–10, the sample wells are designed to closely mate with the conical side walls of the openings 326 in the sample block, particularly after the heated cover applies a downward force on the sample well tray. Upon closing the cover so that a platen of the cover presses onto the top of the sample well tray, any gaps between the outer surface of the sample wells and the openings 326 in the sample block may be greatly reduced or eliminated altogether. The close mating of the sample wells 330 into the sample block openings 326 after the closing of the cover enhances the heat transfer rate between the sample block 314 and the sample well tray 322.

As described for the previous embodiments, when the sample well tray is urged downward by the heated cover, there is a tendency for the sample well tray to deform so that it closely fits in the sample block. Even after the heated cover is opened, the sample wells 330 of the sample well tray 322 will have a tendency to stick inside of the sample block openings 326. As described in the other embodiments, a significant force may be required to loosen the sample well tray 322 from the sample block 314.

In accordance with the present teachings, the embodiment of FIGS. 14–21 includes an urging mechanism for urging the sample well tray from the sample block. The urging mechanism tends to overcome the aforementioned initial sticking force of the sample well tray in the sample block so that the sample well tray is loosened from the sample block without substantial manual or robotic assistance. In the embodiment of FIGS. 14–21, the urging mechanism includes an annular urging plate 316 and a plurality of spring devices 318 and 320. The plurality of spring devices 318 and 320 are interposed between the sample block 314 and the annular plate 316.

As embodied herein and shown in FIGS. 14–21, the annular urging plate 316 may be configured to abut the bottom surface of the sample well tray when the sample well tray is positioned in the sample block. In the embodiment shown in FIGS. 14–21, the annular plate 316 is a substantially flat annular plate with a central opening 334 (see FIG. 18) that is sized to receive a sample well tray thereon. In the embodiment shown, the opening is substantially rectangular so that the matrix of sample wells 330 of the sample well plate 322 may be placed inside the annular plate and into the sample block openings 326. The annular plate may be any other shape suitable for surrounding the periphery of the sample wells of a sample well tray. In the embodiment shown, the annular plate is one-piece, however it should be understood that the urging plate may be made out of several pieces. The annular plate may be made out of any suitable material such as metal or plastic. In one particular embodiment, the annular plate is made out of metal, for example, aluminum.

The urging mechanism may further comprise a plurality of spring devices interposed between the sample block and the annular plate. An example of suitable types of springs is shown in FIGS. 14–21. The plurality of springs comprise first springs 318 and second springs 320 interposed between the sample block 314 and the annular plate 316. The springs are positioned around an outer peripheral surface of the sample block outside of the rectangular grid of sample block openings 326. The spring devices are configured to contact the bottom surface 359 (see FIG. 16) of the annular plate 316 to urge the annular plate and sample well tray 322 away from the sample block.

The springs of this embodiment, by way of example only, are helical coil springs. The springs are typically selected to impart sufficient force on the annular plate 316 to urge the sample well tray 322 away from and slightly out of the sample block 314 after the cover 312 is opened. It should be understood that any other type of suitable spring device may also be used. In the example shown in FIGS. 14–21, the first springs 318 are sized to be slightly smaller than second springs 320.

In one example of the present teachings, the first springs 318 have a free length of 5.30 mm, wire diameter of 0.32 mm, outside diameter of 2.32 mm, and spring rate of 0.262 kg/mm. During closing of the cover, the first springs 318 each compress 2.30 mm thus imparting an ejecting force of 0.603 kg each. In the same example, the second springs 320 have a free length of 6.35 mm, wire diameter of 0.41 mm, outside diameter of 3.05 mm, and spring rate of 0.312 kg/mm. During closing of the cover, the second springs 320 each compress 2.95 mm thus imparting an ejecting force of 0.920 kg. In the present example, there are four first springs and ten second springs, resulting in a total spring force applied to the annular plate and sample well tray of 11.614 kg. These numbers are by way of example only. As is clear from the above description, a greater or lesser number of springs with different spring constants, shapes and sizes may be desirable in order to vary the upward force imparted by the annular plate on the sample well tray upon opening of the cover.

In the example shown in FIG. 16, the sample block includes a recessed portion 384 with a surface below the top surface 328 of the sample block. The recessed portion 384 surrounds the outer periphery of the sample block. The recesses for the springs and the openings for guide members (described below) may be positioned in the recessed portion 384.

Figure 16:
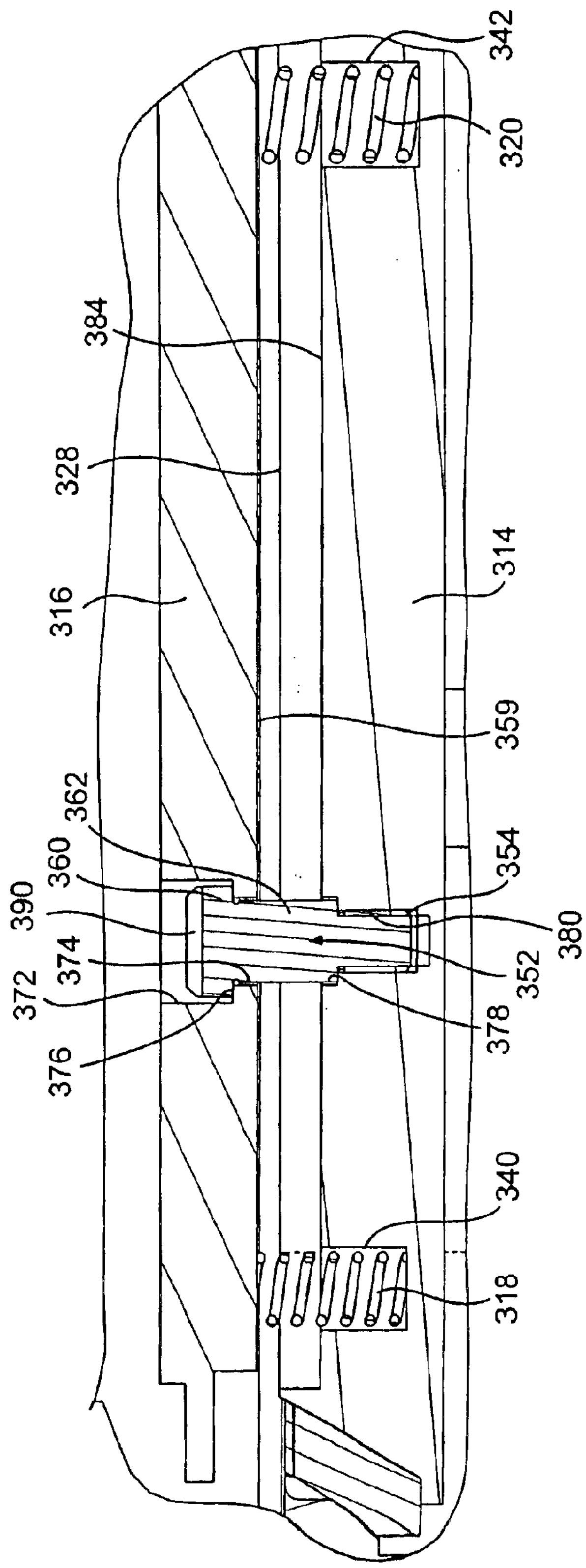
FIG. 16 is a sectional view of the sample block and urging mechanism along line XVI—XVI of FIG. 15.

In the embodiment shown in FIGS. 14–21, the spring devices 318 and 320 are positioned in recesses in the sample block 314. In the embodiment shown, the recesses comprise a first set of cylindrical recesses 340 and a second set of cylindrical recesses 342. The recesses are positioned in an outer peripheral surface of the sample block outside of the rectangular grid of sample block openings 326. In particular, in the example shown in FIG. 16, the recesses 340 and 342 are positioned in the recessed portion 384 of the sample block 314. In the embodiment shown, the first set of cylindrical recesses 340 are sized to accommodate first springs 318, and the second set of cylindrical recesses 342 are sized to accommodate second springs 320. As best shown in the cross-section of FIG. 16, in one embodiment, a first spring 318 is positioned inside the cylindrical recess 340 so that a bottom portion of the first spring 318 is seated in the bottom of the recess 340. As also seen in FIG. 16, a second spring 320 may be positioned inside the cylindrical recess 342 so that a bottom portion of the second spring 320 is seated in the bottom of the recess 342.

Figure 17:
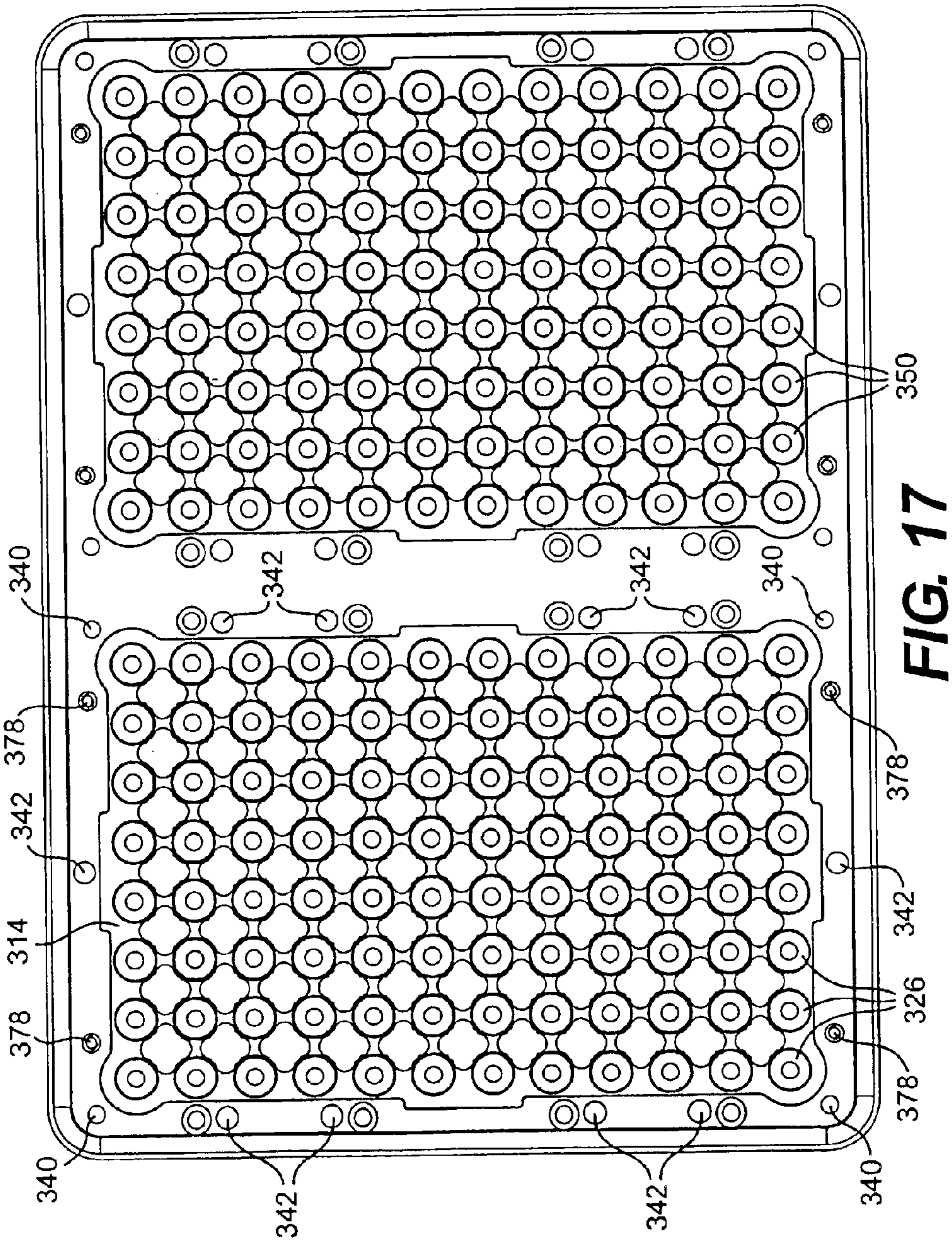
FIG. 17 is a top view of the sample block of FIG. 14 with the annular urging plate removed.
Figure 18:
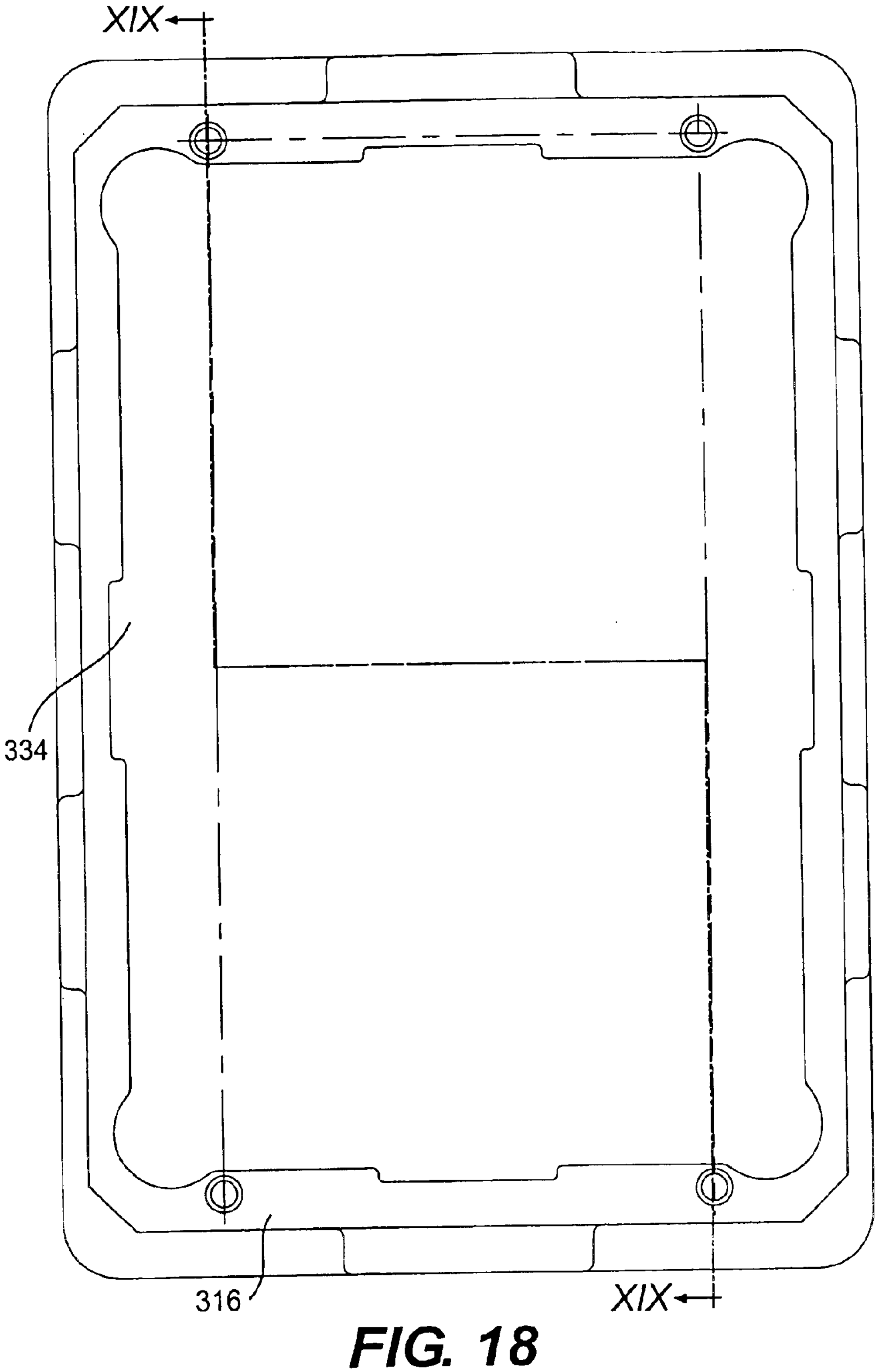
FIG. 18 is a top view of the annular urging plate of FIG. 14.
Figure 19:
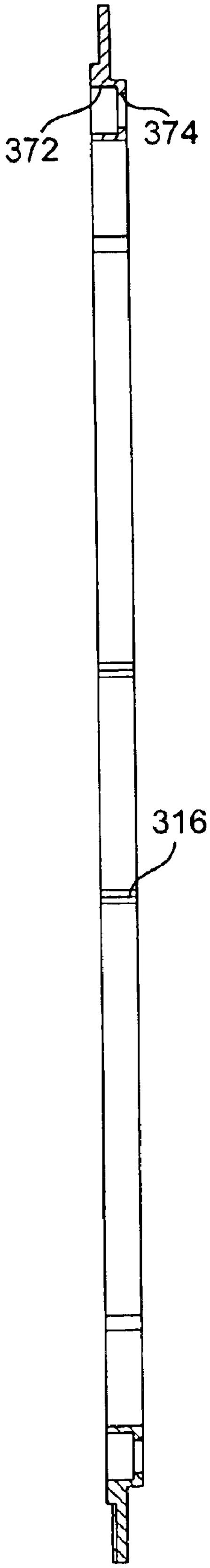
FIG. 19 is a sectional view of the urging plate along line XIX—XIX of FIG. 18.
Figure 20A:
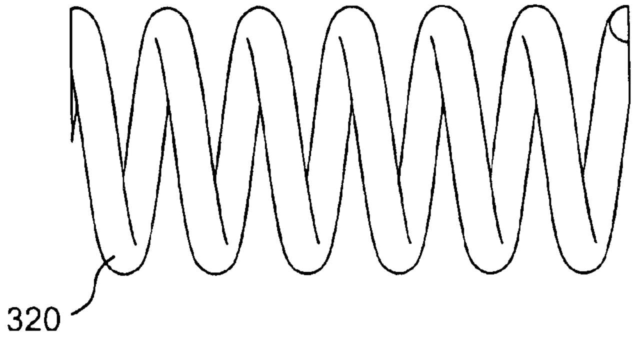
FIGS. 20A, 20B, and 20C are a side view, top view, and a perspective view, respectively, of an ejection spring for the thermal cycler of FIG. 14.
Figure 20B:
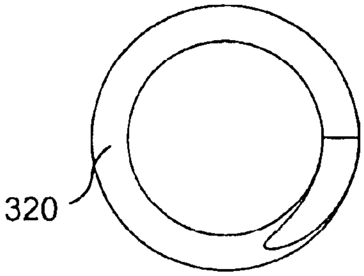
Figure 20C:
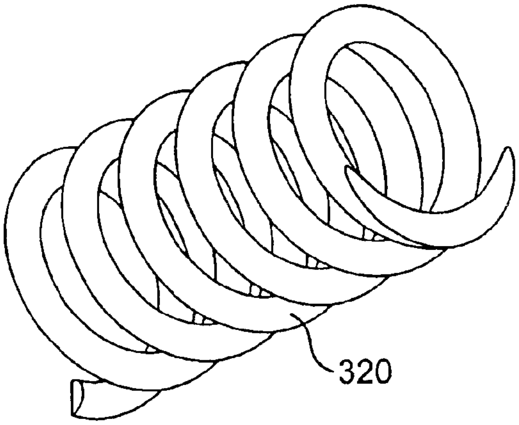
Figure 21A:
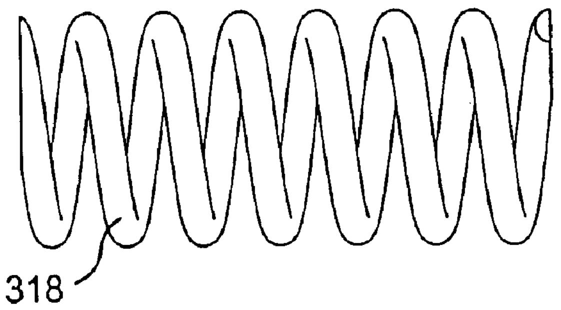
FIGS. 21A, 21B, and 21C are a side view, top view, and a perspective view, respectively, of another ejection spring for the thermal cycler system of FIG. 14.
Figure 21B:
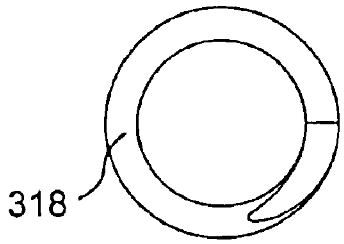
Figure 21C:
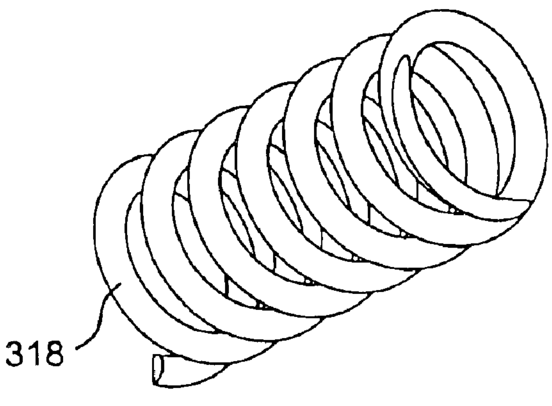

In the embodiment shown in FIGS. 14–21, the springs are symmetrically placed around the periphery of the sample block. The provision of the springs in a symmetrical manner may assist in minimizing undue bending on the sample well tray and ensuring that the force on the annular urging plate is substantially perpendicular to the top surface of the sample block plate. In the embodiment shown, the sample block 314 includes a total of fourteen cylindrical recesses for accommodating the fourteen springs—the first set of recesses 340 totaling four recesses, and the second set of recesses 342 totaling ten recesses. As shown in FIG. 17, four recesses 342 are provided on each longitudinal side (defined as the side with the greater number of sample well openings, for example, the side with twelve sample block openings in FIG. 17) of the first set of sample block openings 326, and two recesses 342 are provided on each lateral side of the first set of sample block openings 326. In the embodiment shown, a recess 340 is provided in each corner of the periphery of the first set of sample block openings 326, for a total of four recesses.

For purposes of ease of discussion, the description below will focus on the set of sample block openings shown on the left side of FIG. 17, for example. It should be understood that the thermal cycling device shown in FIGS. 14–21 is a dual sample well block configuration wherein the sample block includes a second set of sample block openings 350 identical to sample block openings 326. The structure of the second set of sample block openings 350, and their corresponding sample well plate, urging plate, and springs, are roughly identical to that described for the first set of sample block openings 326.

In certain embodiments, the urging mechanism may also include a plurality of guide members for restricting movement of the annular plate in a direction parallel to the upper surface of the sample block. As best shown in FIG. 16, the guide member may comprise a longitudinal shaft 352 configured for permitting movement of the annular urging plate 316 in substantially one direction relative to the sample block 314. In the embodiment shown in FIG. 16, the longitudinal shaft comprises a head portion 360, a middle portion 362, and a threaded portion 364. In the example shown, the head portion 360 has a constant diameter of a first amount, and the middle portion 362 has a constant diameter less than the diameter of the head portion 360. These relative dimensions are for purposes of example only.

In the example shown, the head portion 360 of the longitudinal shaft 352 is positioned in a first cylindrical opening 372 in the annular urging plate. The first cylindrical opening 372 has an inside diameter slightly larger than the diameter of the head portion. The annular plate further includes a second cylindrical opening 374 with a smaller inner diameter than the first cylindrical opening 372. The inner diameter of the second cylindrical opening 374 may be sized to be slightly larger than the diameter of the middle portion 362 of the longitudinal shaft. The junction of the first cylindrical opening 372 and the second cylindrical opening 374 is defined by a stepped surface 376 that may abut the bottom of the head portion 360 when the annular plate 316 is positioned at its farthest distance from the sample block 314. This prevents the annular plate 316 from moving more than a predefined distance from the sample block 314.

In the embodiment shown, the sample block 314 includes a first cylindrical opening 378 and a threaded opening 380 for mating with the threaded portion 354 of the longitudinal shaft. In the example shown, the longitudinal shaft is threaded into the threaded opening 380 to prevent movement of the longitudinal shaft relative to the sample block. The head portion 360 may further include an end surface 390 with a groove configured for receiving the tip of a screwdriver for unscrewing the longitudinal shaft 352 from the sample block. Instead of a threaded portion 354, the longitudinal shaft may be fastened to the sample block by any other suitable method, such as, for example, welding or press fitting. Threads have the advantage of ease of removal and insertion.

The longitudinal shaft 352 is configured to permit the annular plate to move toward and away from the sample block during opening and closing of the heated cover. The guide member provides a movable attachment of the annular plate 316 to the sample block 314, and prevents the annular plate from unintentionally becoming disconnected from the sample block as it is urged upward by the springs 318 and 320.

The present teachings may include a plurality of guide members such as those described above. As shown in FIG. 17, a total of four openings 378 are provided in the sample block for the longitudinal shafts. It should be understood that any number of guide members may be used. The guide member may be any suitable shape for permitting relative movement between the annular urging plate 316 and sample block 314 in the direction perpendicular to the top surface of the sample block. It should be understood that the guide member can be any other type of guide member suitable for permitting relative movement between an annular urging plate and a sample block. The guide member shown in the Figures is for purposes of example only.

The operation of the thermal cycler for one typical embodiment corresponding to FIGS. 14–21 will be described. First, the heated cover of 312 of the thermal cycler is positioned in an open position. The sample well tray 322 is then placed onto the annular plate 316 so that the sample wells 330 align with the sample well block 326. The heated cover may then be moved downward so that it presses against a top surface of the sample well plate, thereby firmly pressing the sample wells of the sample well tray into the openings 326 of the sample block 314. As the heated cover closes, the first and second springs 318 and 320 are compressed by the bottom surface 359 of the annular plate 316 on the outside periphery of the sample wells 330, the annular plate sliding downward relative to the longitudinal shaft. In the embodiment shown in FIG. 16, the bottom portion of the annular plate may be received in the recessed portion 384 when the cover is closed. As the springs are compressed, the springs impart an upward force on the sample well tray 322.

While in the closed position, the thermal cycler 310 may then thermally cycle the liquid sample in the sample well tray to undergo a PCR or other type of chemical reaction. After the thermal cycling and/or other operations are completed, the heated cover 312 is opened (either manually or automatically). As the heated cover is opened, the heated cover (either with or without a platen) will no longer press against the top of the sample well tray. Simultaneously, the springs 318 and 320 will impart an upward force on the bottom surface 359 of the annular urging plate 316, which will then impart an upward force on the sample well tray 322, thereby urging the sample wells 330 out of the sample block openings 326. In one embodiment, the springs impart sufficient force so that the sample well tray 322 will become loosened from the sample block 314 and be raised a slight distance in an upward direction. After the sample well tray is loosened from the sample block, the sample well tray may be manually or robotically lifted out of and away from the sample block without any additional manual steps. As previously discussed, the provision of the urging mechanism allows the sample well tray to be more quickly and efficiently removed from the sample block.

Figure 22:
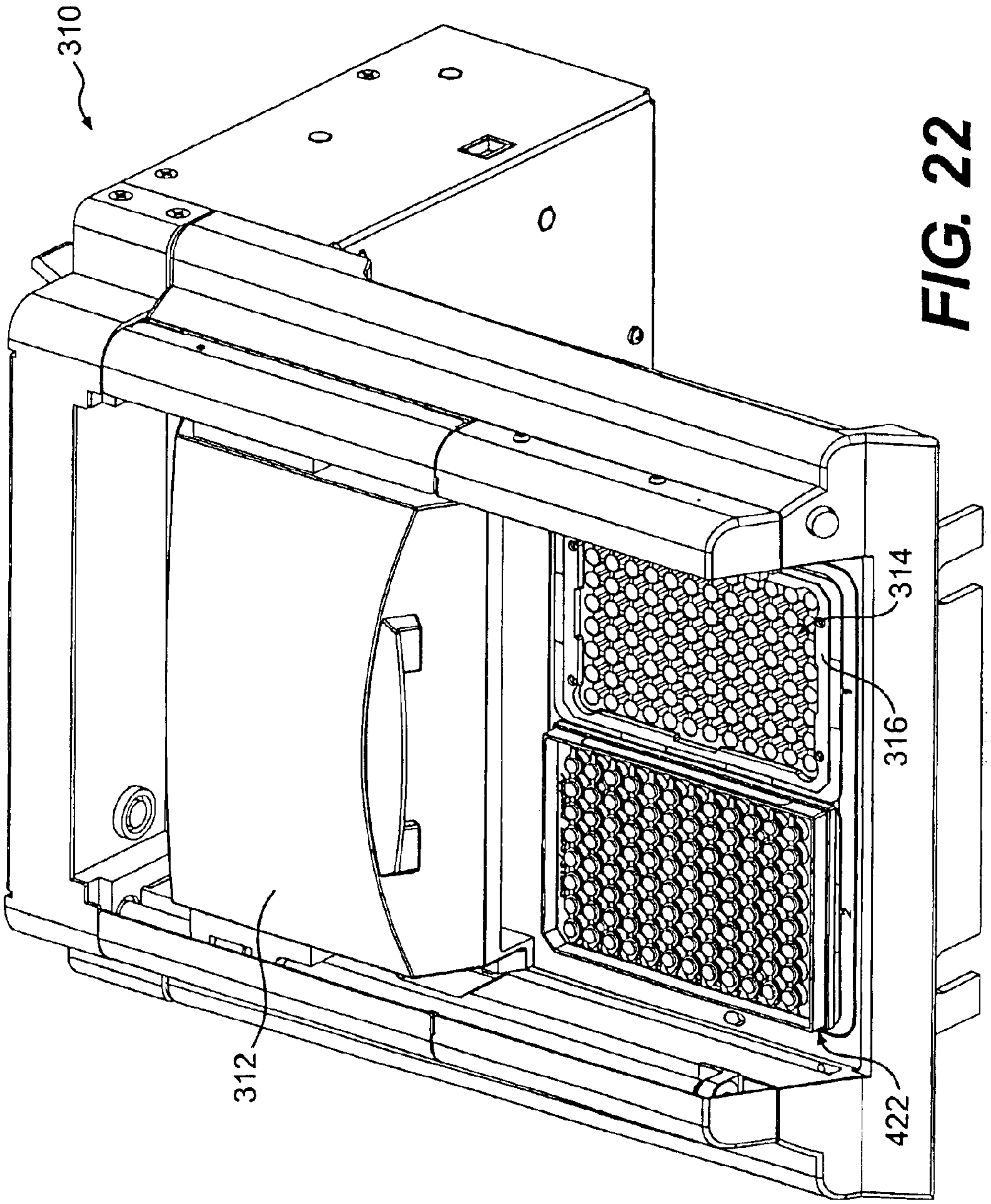
FIG. 22 is a perspective view of the thermal cycler system of FIG. 14 with another type of sample well tray.
Figure 23:
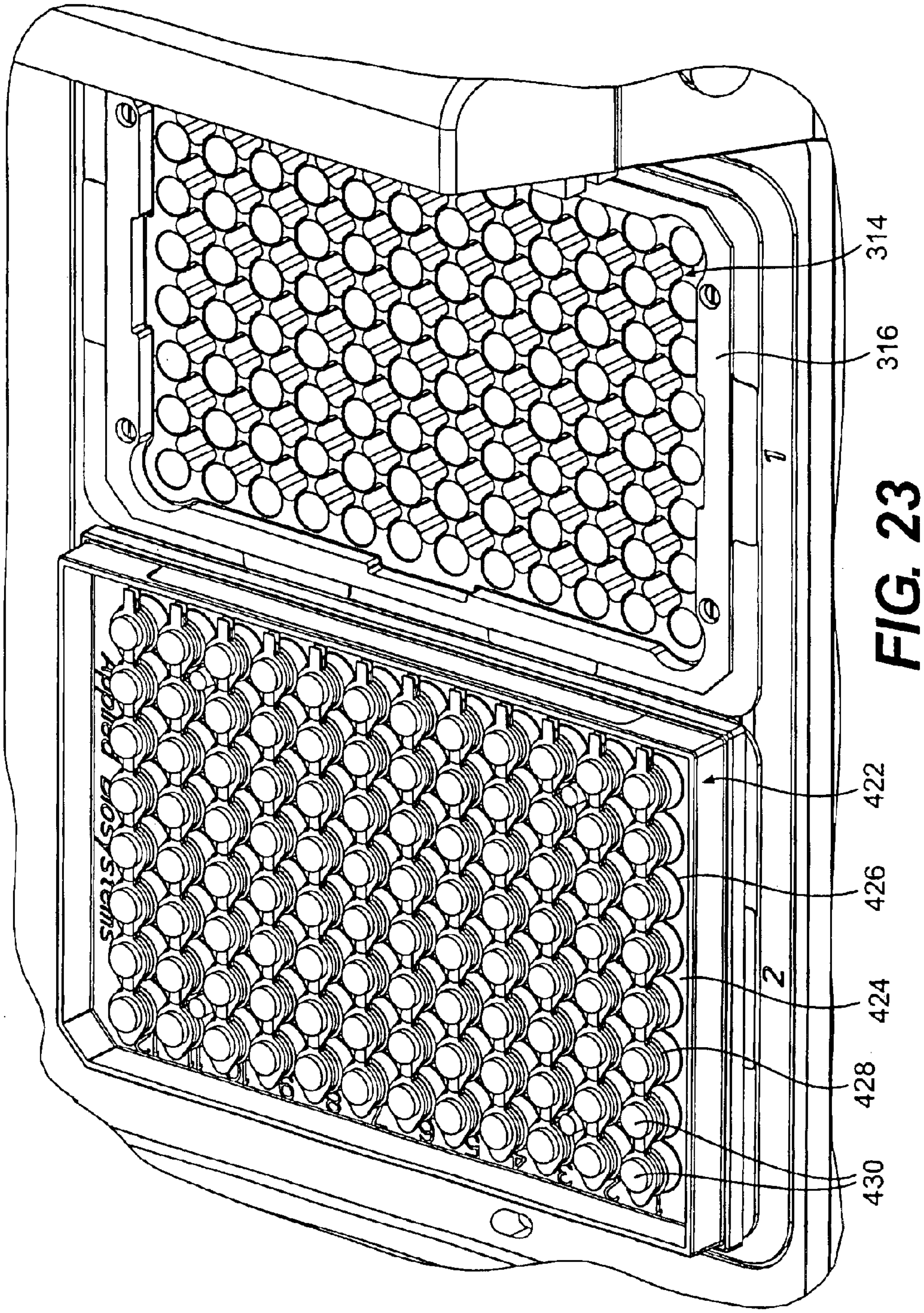
FIG. 23 is a close-up perspective view of a sample block and sample well tray of the system of FIG. 22.

FIGS. 22–23 show the thermal cycler of FIGS. 14–21 with a slightly different sample well tray than described for FIGS. 14–21. In FIGS. 22–23, the thermal cycler 310 comprises the sample block 314, annular urging plate 316, and spring devices (not shown) corresponding to those described in FIGS. 14–21. FIGS. 22–23 show a sample well tray 422 with a tube and cap arrangement. The sample well tray 422 comprises a retainer 424 with a plurality of holes 426. The sample well tray 422 further comprises a plurality of tubes 428 and caps 430 positioned in the holes 426. In the embodiment shown in FIGS. 22–23, the sample well tray 422 is configured to accommodate 96 tubes and caps.

The operation of the thermal cycler 310 of FIGS. 22–23 corresponds to the operation of the thermal cycler in FIGS. 14–21, except that in the operation of the FIGS. 22–23 apparatus, a heated platen from the heated cover will press downward on the caps 430 during the closing of the heated cover. The remainder of the operation corresponds to the operation of the thermal cycler in FIGS. 14–21.

It will be apparent to those skilled in the art that various modifications and variations can be made to the structure and methods described above. For instance, the system could be use in any variety of devices having a plurality of sample wells pressed into a sample block. Thus it should be understood that the present teachings are not limited to the examples discussed in the specification. Rather, the present teachings are intended to cover modifications and variations.

What is claimed is:

1. A thermal cycling device comprising:

a sample block for holding a sample well tray;

a plate adjacent to the sample block;

a plurality of springs positioned under the plate; and a cover that provides a downward force on the sample well tray a closed position;

wherein the plate provides an ejecting force on the sample well tray.

2. The thermal cycling device of claim 1, wherein the springs are helical springs.

3. The thermal cycling device of claim 1, wherein the springs are leaf springs.

4. The thermal cycling device of claim 1, wherein the plate surrounds the outer periphery of the sample block.

5. The thermal cycling device of claim 1, wherein the sample lock provides a plurality of openings for receiving the sample wells.

6. The thermal cycling device of claim 1, wherein plate abuts the bottom surface of the sample well tray.

7. A thermal cycling device comprising:

a sample block for holding a sample well tray;

a plate adjacent to the sample block; and a plurality of springs positioned under the plate;

wherein the sample well tray sticks inside the sample block; and wherein the plate provides an ejecting force on the sample well tray.

8. The thermal cycling device of claim 7, wherein the sample we the tray sticks due to thermal expansion.

9. The thermal cycling device of claim 8, further comprising a cover that provides a downward force on the sample well tray in a closed position, wherein the sample well tray sticks due to the force provided by the cover.

10. A thermal cycling device comprising:

a sample block for holding a sample well tray;

an ejection plate;

a plurality of springs positioned under the ejection plate; and wherein the ejection plate provides a force on the sample well tray wherein the force is adapted to remove the sample well tray with a robotic system.

11. The thermal cycling device of claim 10, wherein the springs are helical springs.

12. The thermal cycling device of claim 10, wherein the springs are leaf springs.

13. The thermal cycling device of claim 10, wherein the ejection plate surrounds the outer periphery of the sample block.

14. The thermal cycling device of claim 10, wherein the sample block provides a plurality of openings for receiving the sample wells.

15. The thermal cycling device of claim 10, wherein ejection plate abuts the bottom surface of the sample well tray.

16. A method for thermal cycling comprising:

positioning in a sample block a sample well tray;

closing a cover to provide a downward force on the sample well tray;

thermally cycling the sample well tray;

opening the cover to remove the downward force on the sample well tray;

ejecting the sample well tray from the sample block with a plate positioned under the sample well tray, wherein a plurality of springs positioned below the plate provide the ejecting;

removing the sample well tray from the sample block.

17. The method for thermal cycling of claim 10, wherein the posit positioning comprises inserting the sample well tray into a plurality of openings in the sample block.

* * * * *